United States Patent
Cegelski et al.

(10) Patent No.: US 11,667,898 B2
(45) Date of Patent: Jun. 6, 2023

(54) PRODUCTION AND USE OF PHOSPHOETHANOLAMINE CELLULOSE AND DERIVATIVES

(71) Applicant: The Board of Trustees of the Leland Stanford Junior University, Stanford, CA (US)

(72) Inventors: Lynette Cegelski, Palo Alto, CA (US); Wiriya Thongsomboon, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 17/308,724

(22) Filed: May 5, 2021

(65) Prior Publication Data
US 2021/0261926 A1    Aug. 26, 2021

Related U.S. Application Data

(62) Division of application No. 16/323,436, filed as application No. PCT/US2017/047511 on Aug. 18, 2017, now abandoned.
(Continued)

(51) Int. Cl.
*C12N 9/10*         (2006.01)
*C12P 19/04*        (2006.01)
(Continued)

(52) U.S. Cl.
CPC ............ *C12N 9/10* (2013.01); *C07K 14/245* (2013.01); *C07K 14/255* (2013.01);
(Continued)

(58) Field of Classification Search
CPC .......... C12N 9/1229; C12N 9/10; C12P 19/04
See application file for complete search history.

(56) References Cited

U.S. PATENT DOCUMENTS 5,268,274 A    12/1993    Ben-Bassat et al.
5,759,828 A    6/1998     Tal et al.
(Continued)

FOREIGN PATENT DOCUMENTS

WO    2015/051203 A1    4/2015

OTHER PUBLICATIONS

Studer. Residue mutations and their impact on protein structure and function: detecting beneficial and pathogenic changes. Biochem. J. (2013) 449, 581-594.*
(Continued)

*Primary Examiner* — Yong D Pak
(74) *Attorney, Agent, or Firm* — Jenny L. Buchbinder; Bozicevic, Field & Francis LLP

(57) ABSTRACT

Phosphoethanolamine cellulose and methods of making and using it are disclosed. In particular, the invention relates to a method of producing a phosphoethanolamine cellulose biosynthetically using a BcsG phosphoethanolamine transferase for cellulose modification. Recombinant constructs encoding BcsG are described, including constructs encoding BcsG by itself or in combination with BcsE and BcsF, which increase the extent of cellulose modification and the amount of modified cellulose produced. Production of phosphoethanolamine cellulose in cell culture and derivatization of phosphoethanolamine cellulose are also described.

19 Claims, 33 Drawing Sheets

Specification includes a Sequence Listing.

Related U.S. Application Data

(60) Provisional application No. 62/376,623, filed on Aug. 18, 2016.

(51) Int. Cl.
*C07K 14/245* (2006.01)
*C12N 9/14* (2006.01)
*C12N 9/12* (2006.01)
*C07K 14/255* (2006.01)
*C08B 3/06* (2006.01)
*C08B 5/02* (2006.01)
*C08B 5/14* (2006.01)
*C08B 11/08* (2006.01)
*C08B 15/06* (2006.01)

(52) U.S. Cl.
CPC ............. *C12N 9/1229* (2013.01); *C12N 9/14* (2013.01); *C12P 19/04* (2013.01); *C08B 3/06* (2013.01); *C08B 5/02* (2013.01); *C08B 5/14* (2013.01); *C08B 11/08* (2013.01); *C08B 15/06* (2013.01); *C12Y 201/01103* (2013.01)

(56) References Cited

U.S. PATENT DOCUMENTS

| | | | |
|---|---|---|---|
| 6,171,614 | B1 | 1/2001 | Chaikof et al. |
| 2004/0146972 | A1 | 7/2004 | Sorge et al. |
| 2008/0181938 | A1 | 7/2008 | Kaspar |
| 2012/0043275 | A1 | 2/2012 | Montemagno et al. |
| 2014/0287024 | A1 | 9/2014 | Wang et al. |
| 2015/0140612 | A1 | 5/2015 | Chen et al. |

OTHER PUBLICATIONS

Thongsomboon. Phosphoethanolamine cellulose: A naturally produced chemically modified cellulose Science. Jan. 19, 2018;359(6373):334-33.*
Anderson (The *Escherichia coli* cellulose synthase subunit G (BcsG) is a Zn2+-dependent phosphoethanolamine transferase. J. Biol. Chem. (2020) 295(18), 6225-6235.*
BCSE_ECOLI. UniProtKB Database. 2015.
BCSF ECOLI. UniProtKB Database. 2015.
BCSG_ECOLI. UniProtKB Database. 2015.
Extended European search report dated Mar. 27, 2020.
Fang et al. (2014) "GIL, a new c-di-GMP-binding protein domain involved in regulation of cellulose synthesis in enterobacteria: GIL, a new c-di-GMP-binding domain.", Mol Microbiol, 93(3):439-452. x.
Galperin et al. (2012) "Divergence and Convergence in Enzyme Evolution," Journal of Biological Chemistry, 287:21-28.
Jahn et al., (2008) "A horizontally acquired cellulose synthase operon in Dickeya dadantii contributes to biofilm formation and attachment to plants.", APS Abstract of Presentation, 1 page.
Jenal et al., (2017) "Cyclic Di-GMP: Second Messenger Extraordinaire", Nature Reviews Microbiology, 271-284.
Jones et al., (2015) "C-di-GMP Regulates Motile to Sessile Transition by Modulating MshA Pili Biogenesis and Near-Surface Motility Behavior in Vibrio cholerae," PLoS Pathog, 11:1-27, e1005068.
Kim et al. (2006) Phosphoethanolamine substitution in the lipid A of *Escherichia coli* 0157:H7 and its association with PmrC. Microbiology 152(Pt3):657-666.
Klein et al. (2013) Molecular and Structural Basis of Inner Core Lipopolysaccharide Alterations in *Escherichia coli* Incorporation of Glucuronic Acid and Phosphoethanolamine in the Heptose Region. J Biol Chem 288(12):8111-8127.
Klemm et al., (2005) "Cellulose: Fascinating Biopolymer and Sustainable Raw Material", Angew. Chem. Int. Ed., 3358-3393.
McCrate et al. (2013) Sum of the Parts: Composition and Architecture of the Bacterial Extracellular Matrix J. Mol Biol 425(22):4286-4294.
Morgan et al., (2014) "Mechanism of activation of bacterial cellulose synthase by cyclic-di-GMP", Nat Struct Mol Biol., 21(5)489-496.
Nishiyama et al., (2003) "Crystal Structure and Hydrogen Bonding System in Cellulose Ialpha from Synchrotron X-ray and Neutron Fiber Diffraction", J. Am. Chem. Soc., 14300-14306.
Omadjela et al., (2013) "BcsA and BcsB form the catalytically active core of bacterial cellulose synthase sufficient for in vitro cellulose synthesis", PLoS, 1-5.
Reynolds et al. (2005) A Phosphoethanolamine Transferase Specific for the Outer 3-deoxy-D-manno-octulosonic Acid Residue of *Escherichia coli* Lipopolysaccharide. Identification of the eptB Gene and Ca2+ Hypersensitivity of an eptB Deletion Mutant. J Biol Chem. 280(22):21202-21211.
Romling et al. (2015) "Bacterial Cellulose Biosynthesis: Diversity of Operons, Subunits, Products and Functions,", Trends Microbiol, 23(9):545-547.
Solano et al., (2002) "Genetic analysis of *Salmonella enteritidis* biofilm formation: critical role of cellulose.", Molecular Microbiology, 43(3):793-808.
Tamayo et al. (2005) Identification of cptA, a PmrA-Regulated Locus Required for Phosphoethanolamine Modification of the *Salmonella enterica* Serovar Typhimurium Lipopolysaccharide Core. J. Bacteriol. 187(10):3391-3399.
Wong et al. (1990) Genetic Organization of the Cellulose Synthase Operon in Acetobacter Xylinum. Proc Natl Acad Sci U.S.A. 87(20):8130-8134.

* cited by examiner

Wild Type　　　　bcsG mutant

SEQUENCE LISTING

<160> NUMBER OF SEQ ID NOS: 13

<210> SEQ ID NO 1
<211> LENGTH: 28
<212> TYPE: DNA
<213> ORGANISM: Artificial Sequence
<220> FEATURE:
<223> OTHER INFORMATION: FMO-68 (HindIII) primer
<220> FEATURE:
<221> NAME/KEY: source
<222> LOCATION: (1)..(28)
<223> OTHER INFORMATION: sequence is synthesized

<400> SEQUENCE: 1
taaataagct tcggacacca gaaatgcc                    28

```
<210> SEQ ID NO 2
<211> LENGTH: 32
<212> TYPE: DNA
<213> ORGANISM: Artificial Sequence
<220> FEATURE:
<223> OTHER INFORMATION: FMO-69 (EcoRV) primer
<220> FEATURE:
<221> NAME/KEY: source
<222> LOCATION: (1)..(32)
<223> OTHER INFORMATION: sequence is synthesized

<400> SEQUENCE: 2
taaatgatat cttaagtctg gttgctaaca gc                                   32

<210> SEQ ID NO 3
<211> LENGTH: 33
<212> TYPE: DNA
<213> ORGANISM: Artificial Sequence
<220> FEATURE:
<223> OTHER INFORMATION: bcsEFG-BamHI primer
<220> FEATURE:
<221> NAME/KEY: source
<222> LOCATION: (1)..(33)
<223> OTHER INFORMATION: sequence is synthesized

<400> SEQUENCE: 3
ggcccgggat ccctggaaga tatagcctat cgc                                  33

<210> SEQ ID NO 4
<211> LENGTH: 31
<212> TYPE: DNA
<213> ORGANISM: Artificial Sequence
<220> FEATURE:
<223> OTHER INFORMATION: bcsF+3-phoA-HindIII primer
<220> FEATURE:
<221> NAME/KEY: source
<222> LOCATION: (1)..(31)
<223> OTHER INFORMATION: sequence is synthesized

<400> SEQUENCE: 4
ggcccgaagc ttcatgatga gcgctccaca g                                    31

<210> SEQ ID NO 5
<211> LENGTH: 32
<212> TYPE: DNA
<213> ORGANISM: Artificial Sequence
<220> FEATURE:
<223> OTHER INFORMATION: bcsF+72-phoA-HindIII primer
<220> FEATURE:
<221> NAME/KEY: source
<222> LOCATION: (1)..(32)
<223> OTHER INFORMATION: sequence is synthesized

<400> SEQUENCE: 5
ggcccgaagc ttcagatagc ccagcgggaa aa                                   32

<210> SEQ ID NO 6
<211> LENGTH: 32
<212> TYPE: DNA
<213> ORGANISM: Artificial Sequence
<220> FEATURE:
<223> OTHER INFORMATION: bcsG+3-phoA-HindIII primer
<220> FEATURE:
<221> NAME/KEY: source
<222> LOCATION: (1)..(32)
<223> OTHER INFORMATION: sequence is synthesized

<400> SEQUENCE: 6
ggcccgaagc ttcatttttt ggttgccctg gc                                   32
```

```
<210> SEQ ID NO 7
<211> LENGTH: 31
<212> TYPE: DNA
<213> ORGANISM: Artificial Sequence
<220> FEATURE:
<223> OTHER INFORMATION: bcsG+474-phoA-HindIII primer
<220> FEATURE:
<221> NAME/KEY: source
<222> LOCATION: (1)..(31)
<223> OTHER INFORMATION: sequence is synthesized

<400> SEQUENCE: 7
ggcccgaagc ttacttggtc ccgccagggt a                               31

<210> SEQ ID NO 8
<211> LENGTH: 32
<212> TYPE: DNA
<213> ORGANISM: Artificial Sequence
<220> FEATURE:
<223> OTHER INFORMATION: bcsF+4-lacZ-HindIII primer
<220> FEATURE:
<221> NAME/KEY: source
<222> LOCATION: (1)..(32)
<223> OTHER INFORMATION: sequence is synthesized

<400> SEQUENCE: 8
ggcccgaagc tttcatgatg agcgctccac ag                              32

<210> SEQ ID NO 9
<211> LENGTH: 31
<212> TYPE: DNA
<213> ORGANISM: Artificial Sequence
<220> FEATURE:
<223> OTHER INFORMATION: bcsF+73-lacZ-HindIII primer
<220> FEATURE:
<221> NAME/KEY: source
<222> LOCATION: (1)..(31)
<223> OTHER INFORMATION: sequence is synthesized

<400> SEQUENCE: 9
ggcccgaagc ttccagatag cccagcggga a                               31

<210> SEQ ID NO 10
<211> LENGTH: 33
<212> TYPE: DNA
<213> ORGANISM: Artificial Sequence
<220> FEATURE:
<223> OTHER INFORMATION: bcsG+4-lacZ-HindIII primer
<220> FEATURE:
<221> NAME/KEY: source
<222> LOCATION: (1)..(33)
<223> OTHER INFORMATION: sequence is synthesized

<400> SEQUENCE: 10
ggcccgaagc tttcattttt tggttgccct ggc                             33

<210> SEQ ID NO 11
<211> LENGTH: 33
<212> TYPE: DNA
<213> ORGANISM: Artificial Sequence
<220> FEATURE:
<223> OTHER INFORMATION: bcsG+487-lacZ-HindIII primer
<220> FEATURE:
<221> NAME/KEY: source
<222> LOCATION: (1)..(33)
<223> OTHER INFORMATION: sequence is synthesized

<400> SEQUENCE: 11
ggcccgaagc ttgccacaag gagaaacttg gtc                             33
```

-continued

```
<210> SEQ ID NO 12
<211> LENGTH: 559
<212> TYPE: PRT
<213> ORGANISM: Escherichia coli
<300> PUBLICATION INFORMATION:
<308> DATABASE ACCESSION NUMBER: NCBI/NP_417995
<309> DATABASE ENTRY DATE: 2016-08-08
<313> RELEVANT RESIDUES IN SEQ ID NO: (1)..(559)

<400> SEQUENCE: 12

Met Thr Gln Phe Thr Gln Asn Thr Ala Met Pro Ser Ser Leu Trp Gln
1               5                   10                  15

Tyr Trp Arg Gly Leu Ser Gly Trp Asn Phe Tyr Phe Leu Val Lys Phe
            20                  25                  30

Gly Leu Leu Trp Ala Gly Tyr Leu Asn Phe His Pro Leu Leu Asn Leu
        35                  40                  45

Val Phe Ala Ala Phe Leu Leu Met Pro Leu Pro Arg Tyr Ser Leu His
    50                  55                  60

Arg Leu Arg His Trp Ile Ala Leu Pro Ile Gly Phe Ala Leu Phe Trp
65                  70                  75                  80

His Asp Thr Trp Leu Pro Gly Pro Glu Ser Ile Met Ser Gln Gly Ser
                85                  90                  95

Gln Val Ala Gly Phe Ser Thr Asp Tyr Leu Ile Asp Leu Val Thr Arg
            100                 105                 110

Phe Ile Asn Trp Gln Met Ile Gly Ala Ile Phe Val Leu Leu Val Ala
        115                 120                 125

Trp Leu Phe Leu Ser Gln Trp Ile Arg Ile Thr Val Phe Val Val Ala
    130                 135                 140

Ile Leu Leu Trp Leu Asn Val Leu Thr Leu Ala Gly Pro Ser Phe Ser
145                 150                 155                 160

Leu Trp Pro Ala Gly Gln Pro Thr Thr Val Thr Thr Gly Gly
                165                 170                 175

Asn Ala Ala Ala Thr Val Ala Ala Thr Gly Gly Ala Pro Val Val Gly
            180                 185                 190

Asp Met Pro Ala Gln Thr Ala Pro Pro Thr Thr Ala Asn Leu Asn Ala
        195                 200                 205

Trp Leu Asn Asn Phe Tyr Asn Ala Glu Ala Lys Arg Lys Ser Thr Phe
    210                 215                 220

Pro Ser Ser Leu Pro Ala Asp Ala Gln Pro Phe Glu Leu Leu Val Ile
225                 230                 235                 240

Asn Ile Cys Ser Leu Ser Trp Ser Asp Ile Glu Ala Ala Gly Leu Met
                245                 250                 255

Ser His Pro Leu Trp Ser His Phe Asp Ile Glu Phe Lys Asn Phe Asn
            260                 265                 270

Ser Ala Thr Ser Tyr Ser Gly Pro Ala Ala Ile Arg Leu Leu Arg Ala
        275                 280                 285

Ser Cys Gly Gln Thr Ser His Thr Asn Leu Tyr Gln Pro Ala Asn Asn
    290                 295                 300

Asp Cys Tyr Leu Phe Asp Asn Leu Ser Lys Leu Gly Phe Thr Gln His
305                 310                 315                 320

Leu Met Met Gly His Asn Gly Gln Phe Gly Phe Leu Lys Glu Val
                325                 330                 335

Arg Glu Asn Gly Gly Met Gln Ser Glu Leu Met Asp Gln Thr Asn Leu
            340                 345                 350

Pro Val Ile Leu Leu Gly Phe Asp Gly Ser Pro Val Tyr Asp Asp Thr
        355                 360                 365
```

Ala Val Leu Asn Arg Trp Leu Asp Val Thr Glu Lys Asp Lys Asn Ser
            370                 375                 380

Arg Ser Ala Thr Phe Tyr Asn Thr Leu Pro Leu His Asp Gly Asn His
385                 390                 395                 400

Tyr Pro Gly Val Ser Lys Thr Ala Asp Tyr Lys Ala Arg Ala Gln Lys
                405                 410                 415

Phe Phe Asp Glu Leu Asp Ala Phe Phe Thr Glu Leu Glu Lys Ser Gly
            420                 425                 430

Arg Lys Val Met Val Val Val Pro Glu His Gly Gly Ala Leu Lys
                435                 440                 445

Gly Asp Arg Met Gln Val Ser Gly Leu Arg Asp Ile Pro Ser Pro Ser
450                 455                 460

Ile Thr Asp Val Pro Val Gly Val Lys Phe Phe Gly Met Lys Ala Pro
465                 470                 475                 480

His Gln Gly Ala Pro Ile Val Ile Glu Gln Pro Ser Ser Phe Leu Ala
                485                 490                 495

Ile Ser Asp Leu Val Val Arg Val Leu Asp Gly Lys Ile Phe Thr Glu
            500                 505                 510

Asp Asn Val Asp Trp Lys Lys Leu Thr Ser Gly Leu Pro Gln Thr Ala
            515                 520                 525

Pro Val Ser Glu Asn Ser Asn Ala Val Val Ile Gln Tyr Gln Asp Lys
530                 535                 540

Pro Tyr Val Arg Leu Asn Gly Gly Asp Trp Val Pro Tyr Pro Gln
545                 550                 555

<210> SEQ ID NO 13
<211> LENGTH: 559
<212> TYPE: PRT
<213> ORGANISM: Salmonella enterica
<300> PUBLICATION INFORMATION:
<308> DATABASE ACCESSION NUMBER: NCBI/WP_085347572
<309> DATABASE ENTRY DATE: 2017-04-26
<313> RELEVANT RESIDUES IN SEQ ID NO: (1)..(559)

<400> SEQUENCE: 13

Met Thr Gln His Thr Gln Thr Pro Ser Met Pro Ser Pro Leu Trp Gln
1               5                   10                  15

Tyr Trp Arg Gly Leu Ser Gly Trp Asn Phe Tyr Phe Leu Val Lys Phe
            20                  25                  30

Gly Leu Leu Trp Ala Gly Tyr Leu Asn Phe His Pro Leu Leu Asn Leu
        35                  40                  45

Val Phe Met Ala Phe Leu Leu Ile Pro Ile Pro Lys Tyr Arg Leu His
50                  55                  60

Gln Leu Arg His Trp Ile Ala Ile Pro Val Gly Phe Ala Leu Phe Trp
65                  70                  75                  80

His Asp Thr Trp Leu Pro Gly Pro Gln Ser Ile Met Ser Gln Gly Thr
                85                  90                  95

Gln Val Ala Glu Phe Ser Ser Gly Tyr Leu Leu Asp Leu Ile Ala Arg
            100                 105                 110

Phe Ile Asn Trp Gln Met Ile Gly Ala Val Phe Val Leu Leu Val Ala
        115                 120                 125

Trp Leu Phe Leu Ser Gln Trp Ile Arg Val Thr Val Phe Val Val Ala
130                 135                 140

Ile Met Val Trp Leu Asn Val Leu Thr Leu Thr Gly Pro Val Phe Thr
145                 150                 155                 160

```
Leu Trp Pro Ala Gly Gln Pro Thr Asp Thr Val Thr Thr Gly Gly
                165                 170                 175

Asn Ala Ala Ala Thr Val Ala Thr Ala Gly Asp Lys Pro Ile Ile Gly
                180                 185                 190

Asp Met Pro Ala Gln Thr Ala Pro Pro Thr Thr Ala Asn Met Asn Ala
            195                 200                 205

Trp Leu Asn Thr Phe Tyr Thr Ala Glu Glu Lys Arg Lys Thr Thr Phe
        210                 215                 220

Pro Ala Gln Leu Pro Pro Asp Ala Gln Pro Phe Asp Leu Leu Val Ile
225                 230                 235                 240

Asn Ile Cys Ser Leu Ser Trp Ser Asp Val Glu Ala Ala Gly Leu Met
                245                 250                 255

Ser His Pro Leu Trp Ser His Phe Asp Ile Leu Phe Lys His Phe Asn
                260                 265                 270

Ser Gly Thr Ser Tyr Ser Gly Pro Ala Ala Ile Arg Leu Leu Arg Ala
                275                 280                 285

Ser Cys Gly Gln Pro Ser His Thr Arg Leu Tyr Gln Pro Ala Asp Asn
        290                 295                 300

Glu Cys Tyr Leu Phe Asp Asn Leu Ala Lys Leu Gly Phe Thr Gln His
305                 310                 315                 320

Leu Met Met Asp His Asn Gly Glu Phe Gly Gly Phe Leu Lys Glu Val
                325                 330                 335

Arg Glu Asn Gly Gly Met Gln Ser Glu Leu Met Asn Gln Ser Gly Leu
                340                 345                 350

Pro Thr Ala Leu Leu Ser Phe Asp Gly Ser Pro Val Tyr Asp Asp Leu
        355                 360                 365

Ala Val Leu Asn Arg Trp Leu Thr Gly Glu Glu Arg Glu Ala Asn Ser
        370                 375                 380

Arg Ser Ala Thr Phe Phe Asn Leu Leu Pro Leu His Asp Gly Asn His
385                 390                 395                 400

Phe Pro Gly Val Ser Lys Thr Ala Asp Tyr Lys Ile Arg Ala Gln Lys
                405                 410                 415

Leu Phe Asp Glu Leu Asp Ala Phe Phe Thr Glu Leu Glu Lys Ser Gly
                420                 425                 430

Arg Lys Val Met Val Val Val Pro Glu His Gly Gly Ala Leu Lys
                435                 440                 445

Gly Asp Arg Met Gln Ile Ser Gly Leu Arg Asp Ile Pro Ser Pro Ser
450                 455                 460

Ile Thr Asn Val Pro Ala Gly Val Lys Phe Phe Gly Met Lys Ala Pro
465                 470                 475                 480

His Glu Gly Ala Pro Ile Asp Ile Asn Gln Pro Ser Ser Tyr Leu Ala
                485                 490                 495

Ile Ser Glu Leu Val Val Arg Ala Val Asp Gly Lys Leu Phe Thr Glu
                500                 505                 510

Asp Ser Val Asn Trp Asn Lys Leu Thr Ser Asn Leu Pro Gln Thr Ala
            515                 520                 525

Pro Val Ser Glu Asn Ala Asn Ala Val Ile Gln Tyr Gln Gly Lys
        530                 535                 540

Pro Tyr Val Arg Leu Asn Gly Gly Asp Trp Val Pro Tyr Pro Gln
545                 550                 555
```

PRODUCTION AND USE OF PHOSPHOETHANOLAMINE CELLULOSE AND DERIVATIVES

CROSS-REFERENCE TO RELATED APPLICATIONS

This application is a divisional application of U.S. application Ser. No. 16/323,436, filed Feb. 5, 2019, which is the National Stage of International Application No. PCT/US2017/047511, filed Aug. 18, 2017, which claims benefit under 35 U.S.C. § 119(e) of provisional application Ser. No. 62/376,623, filed Aug. 18, 2016, all of which applications are hereby incorporated by reference in their entireties.

FEDERALLY SPONSORED RESEARCH AND DEVELOPMENT

This invention was made with Government support under contract 1453247 awarded by the National Science Foundation. The Government has certain rights in the invention.

TECHNICAL FIELD

The present invention relates to modified celuloses and their use. In particular, the invention relates to compositions and methods of producing phosphoethanolamine cellulose and derivatives thereof.

BACKGROUND

Cellulose is the most abundant biopolymer on earth. Plants rely on the tensile strength and mechanical properties of cellulose to stand tall (Klemm et al. (2005) Angew Chem. Int. Ed. 44, 3358-3393). Chemically, cellulose is a linear polysaccharide composed of β-1,4 linked glucose. Individual strands participate in strong hydrogen bonding networks with neighboring strands and contribute to the physical and chemical integrity of plant cell walls and cellulosic materials (Nishiyama et al. (2003) J. Am. Chem. Soc. 125, 14300-14306). Microorganisms are also major producers of cellulose (Romling et al. (2015) Trends Microbiol. 23, 545-557).

The essential genetic and protein machinery for cellulose production in bacteria includes the cellulose synthase genes, termed bcsA and bcsB, encoding cellulose synthase subunits, BcsA and BcsB (Omadjela et al. (2013) Proc. Natl. Acad. Sci. USA 110, 17856-17861). BcsA is an integral membrane protein containing the catalytic active site. BcsB interacts with BcsA at the periplasmic face of the inner membrane in Gram-negative bacteria, with the two subunits forming a channel for co-synthetic secretion of cellulose. Cellulose biosynthesis requires activation by the ubiquitous bacterial second messenger cyclic di-GMP (Jenal et al. (2017) Nat. Rev. Microbiol. 15, 271-284) which directly binds to BcsA (Morgan et al. (2014) Nat. Struct. Mol. Biol 21, 489-496). Intense curiosity has emerged in understanding the diversity of additional genes in cellulose biosynthesis operons present in many microorganisms (Romling et al., supra).

SUMMARY

The invention relates to phosphoethanolamine cellulose and its use as well as methods of producing phosphoethanolamine cellulose and derivatives thereof.

In one aspect, the invention includes a cellulose-producing host cell comprising a recombinant polynucleotide encoding a BcsG phosphoethanolamine transferase operably linked to a promoter.

In certain embodiments, the recombinant polynucleotide is provided by a plasmid or viral vector.

In other embodiments, the recombinant nucleic acid is integrated into the host cell genome.

In another embodiment, the host cell further comprises a recombinant polynucleotide comprising a BcsE gene and/or a BcsF gene operably linked to a promoter.

In another embodiment, the recombinant polynucleotide comprises a multicistronic vector expressing BcsG, BcsE, and BcsF. The multicistronic vector may comprise, for example, a polynucleotide encoding an internal ribosome entry site (IRES) or a T2A peptide.

In another embodiment, the recombinant polynucleotide comprises a bcsEFG operon.

In certain embodiments, the host cell is a bacterial cell, a plant cell, or an algae cell. For example, the cellulose-producing host cell may be a Gram-negative bacterium. Exemplary Gram-negative bacteria include those belonging to the *Acetobacter* (e.g., *Acetobacter xylinum*), *Agrobacterium, Escherichia* (e.g., *Escherichia coli*), and *Salmonella* (e.g., *Salmonella enterica*) genuses.

In another embodiment, cellulose production is upregulated by cyclic di-GMP, for example, by adding cyclic di-GMP to the cell.

In another embodiment, the cellulose-producing host cell further comprises a recombinant polynucleotide comprising a promoter operably linked to a polynucleotide encoding diguanylate cyclase. The promoter may be an inducible promoter. The recombinant polynucleotide may be provided by a vector such as a plasmid or viral vector.

In another aspect, the invention includes a method of producing a phosphoethanolamine cellulose, the method comprising: a) culturing a cellulose-producing host cell comprising a recombinant polynucleotide encoding a BcsG phosphoethanolamine transferase operably linked to a promoter under conditions suitable for expression of the BcsG phosphoethanolamine transferase, wherein the phosphoethanolamine cellulose is produced; and b) isolating the phosphoethanolamine cellulose.

Media may be supplied with a continuous or batch fed system. In certain embodiments, culturing is performed in a growth media comprising one or more carbon sources selected from the group consisting of glucose, fructose, acetate, or glycerol. In certain embodiments, culturing is performed at a temperature below 30° C. For example, culturing may be performed at a temperature in a range from about 25° C. to about 29° C., or any temperature in between, such as 25° C., 26° C., 27° C., 28° C., or 29° C. In other embodiments, culturing may be performed at a temperature in a range from about 30° C. to about 37° C., or any temperature in between, such as 31° C., 32° C., 33° C., 34° C., 35° C., or 36° C.

In another embodiment, the method further comprises increasing cellulose production by contacting the cellulose-producing host cell with cyclic di-GMP.

In another embodiment, the method further comprises transfecting the cellulose-producing host cell with a recombinant polynucleotide comprising a promoter operably linked to a polynucleotide encoding diguanylate cyclase. The promoter may be an inducible promoter. The recombinant polynucleotide may be provided by a vector such as a plasmid or viral vector.

In another aspect, the invention includes a composition comprising a phosphoethanolamine cellulose ester, wherein at least one hydroxyl group of the phosphoethanolamine cellulose is esterified, for example, with an organic acid, acid anhydride, or acid chloride, or an inorganic acid. Exemplary organic acids include acetic acid, propanoic acid, and butyric acid. Exemplary inorganic acids include nitric acid and sulfuric acid.

In another aspect, the invention includes a composition comprising a phosphoethanolamine cellulose ether, wherein at least one hydroxyl group of the phosphoethanolamine cellulose is etherified. In certain embodiments, the phosphoethanolamine cellulose ether is an alkyl ether, a hydroxyalkyl ether, or a carboxyalkyl ether.

In another aspect, the invention includes a composition comprising a phosphoethanolamine cellulose, wherein at least one amine group is chemically modified. For example, at least one amine group may be alkylated, acylated, or sulfonated. In another embodiment, at least one amine group is conjugated to an agent. In certain embodiments, the agent is a peptide, antibody, enzyme, nucleic acid, dye, ligand, or drug.

In another aspect, the invention includes a method of hydrolyzing a phosphoethanolamine cellulose, the method comprising contacting the phosphoethanolamine cellulose with one or more cellulases. For example, endocellulases, exocellulases, beta-glucosidases, oxidative cellulases, cellulose phosphorylases, or a combination thereof may be used in hydrolysis of a phosphoethanolamine cellulose.

These and other embodiments of the subject invention will readily occur to those of skill in the art in view of the disclosure herein.

BRIEF DESCRIPTION OF THE FIGURES

FIG. 1A shows the chemical structure representation of glucose and pEtN glucose units in pEtN cellulose. FIG. 1B shows the $^{13}$C CPMAS solid-state NMR spectra of the pure cellulosic material isolated without the use of CR in the growth medium (top) and with CR (bottom). The pure CR spectrum is provided as an overlay (dashed gray line). The comparison demonstrates that purification with CR does not influence the polysaccharide composition. FIG. 1C that the C6' and C7 carbon chemical shift region exhibited the strongest dephasing in the 1-ms C{P} REDOR NMR measurement, followed next by the C5' and C8 carbons. FIG. 1D shows the $^{13}$C CPMAS spectrum of the cellulosic material isolated from the bcsG derivative lacked modification carbons and contained only the $^{13}$C chemical shifts expected for standard amorphous cellulose.

FIG. 2A shows isotopic labeling with L-[3-$^{13}$C]serine-supplemented YESCA nutrient medium resulted in enrichment of the pEtN cellulose C7 carbon in an isolated pEtN sample, consistent with routing through a possible substrate such as phosphatidylethanolamine. FIG. 2B shows isotopic labeling with L-[$^{15}$N]serine was evaluated by $^{15}$N CPMAS NMR on ECM samples containing both curli and cellulosic material. Amide $^{15}$N signals correspond to curli amides. The loss of the amine $^{15}$N signal in the bcsG derivative assigned the amine nitrogen to pEtN cellulose. Loss of the modification was accompanied by loss of the wrinkled macrocolony morphology (inset photographs). FIG. 2C shows the $^{13}$C CPMAS spectrum of the cellulosic material isolated from *Salmonella enterica* serovar *Typhimurium* strain IR715ΔcsgBA matched that of pEtN cellulose from AR3110ΔcsgBA.

Figure 1A:
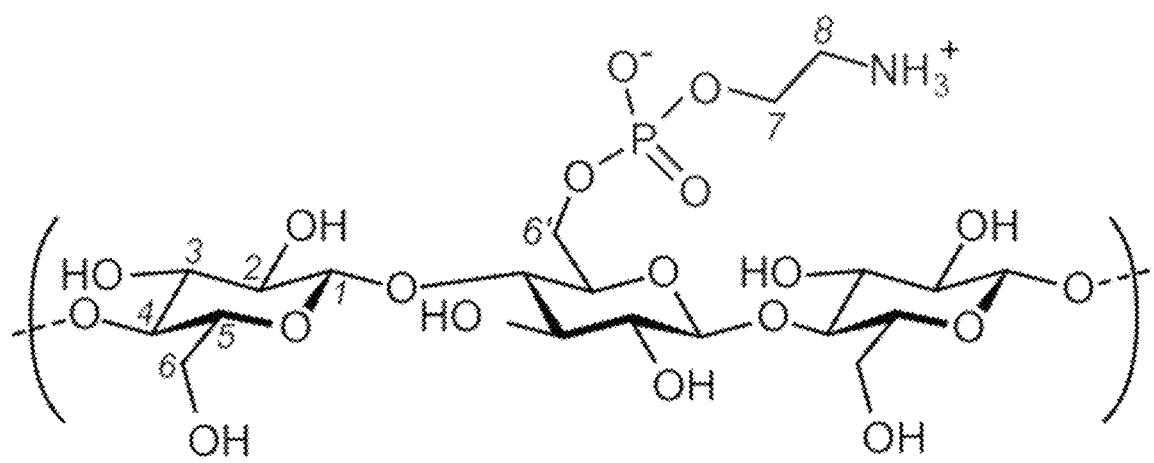
FIG. 1A-1D show that *E. coli* produces phosphoethanolamine cellulose.
Figure 1B:
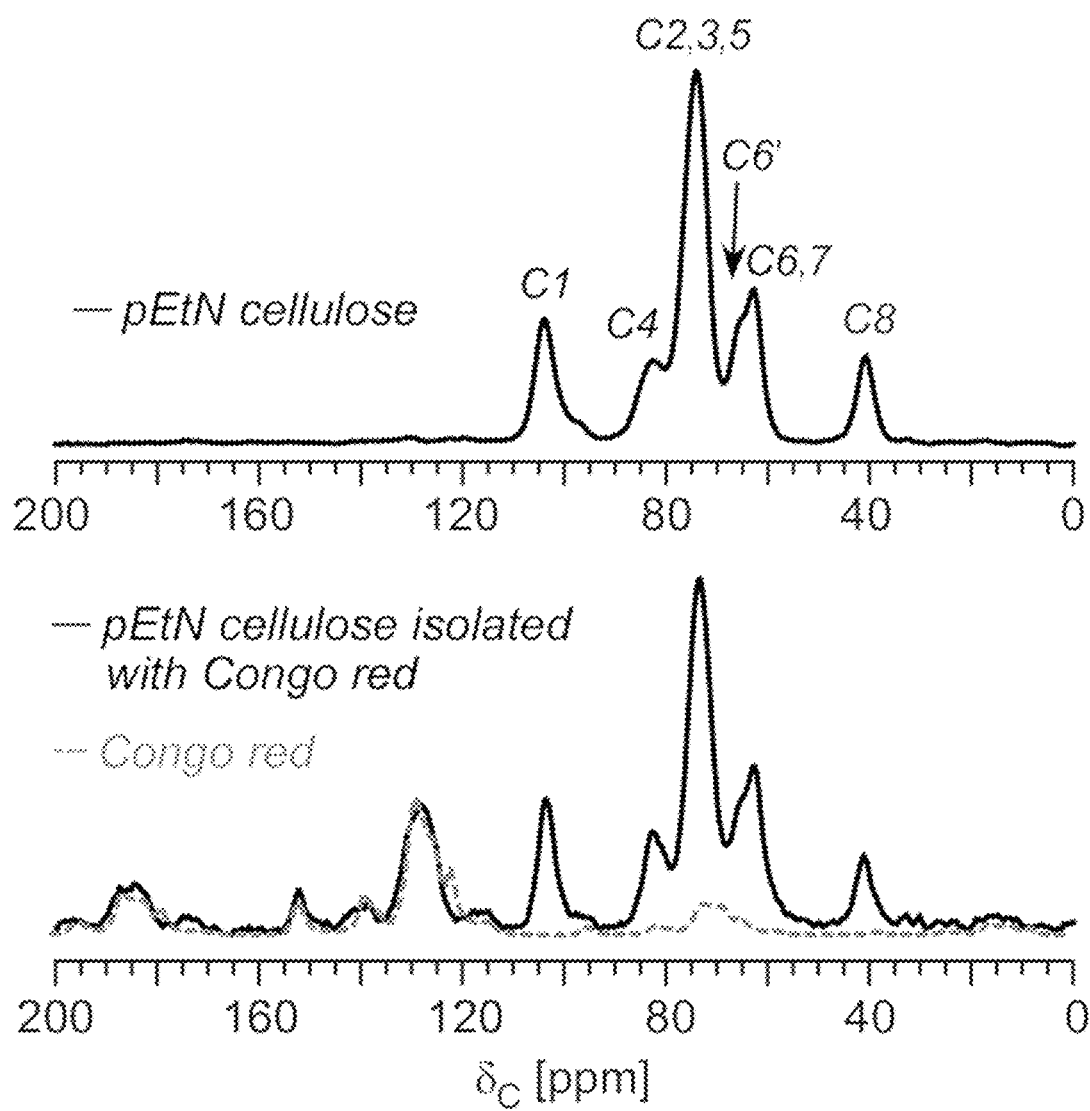
Figure 1C:
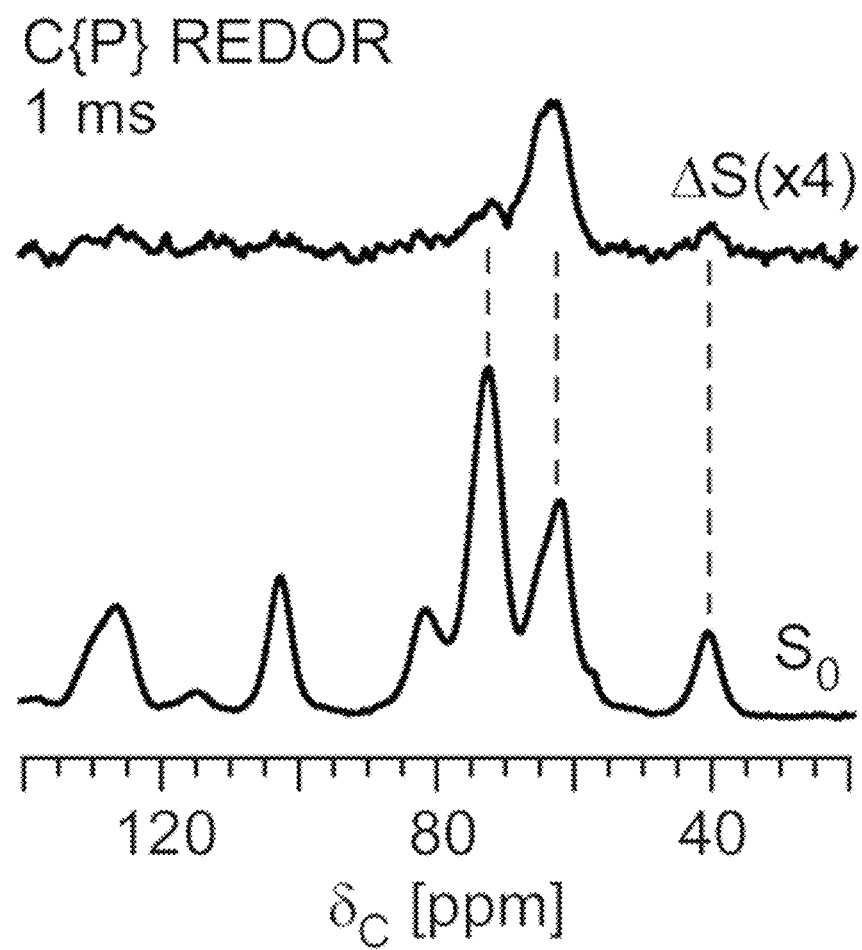

125-MHz $^{13}$C CPMAS NMR was performed on the pure pEtN cellulose sample shown in FIG. 1B (without the inclusion of CR) as a function of the contact time to extract the maximum magnetization through CP transfer without relaxation. The C1 and C8 carbons are the most well resolved and well suited for the quantitative CP measurements. CP behavior, with decay due to T1p, was similar for the C1 and C8 carbons and yielded a C1:C8 ratio of 1.9:1. Thus, approximately one half of the glucose units are modified with the phosphoethanolamine group. Magic-angle spinning was performed at 7143 Hz.

Figure 12:
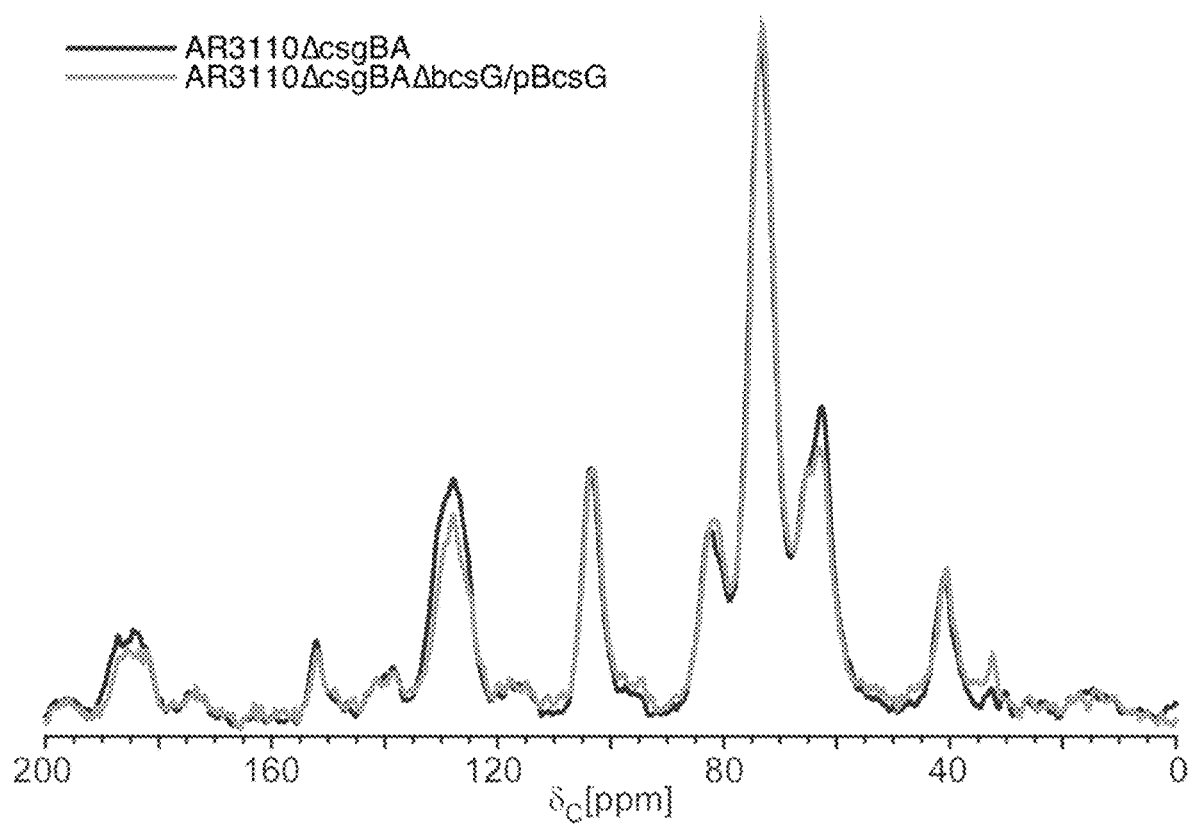
Figure 13A:
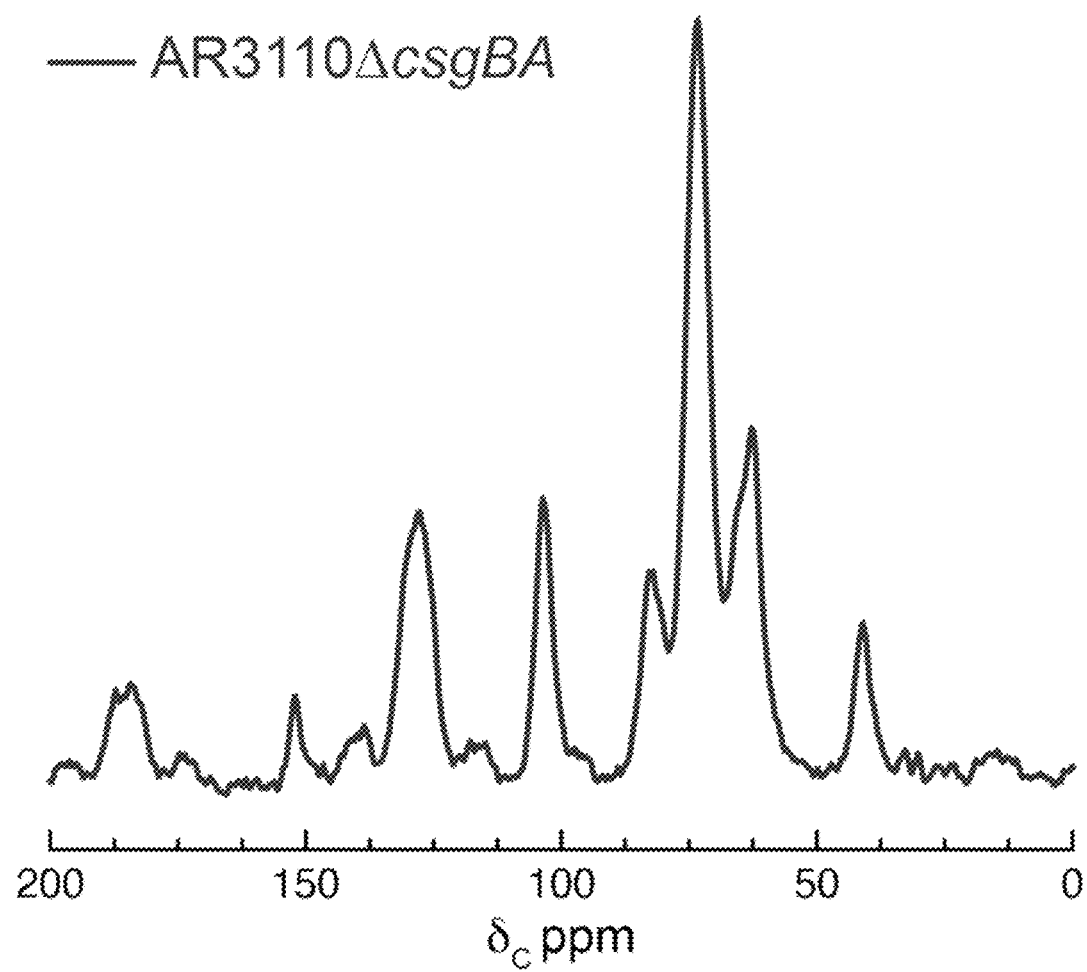
Figure 13B:
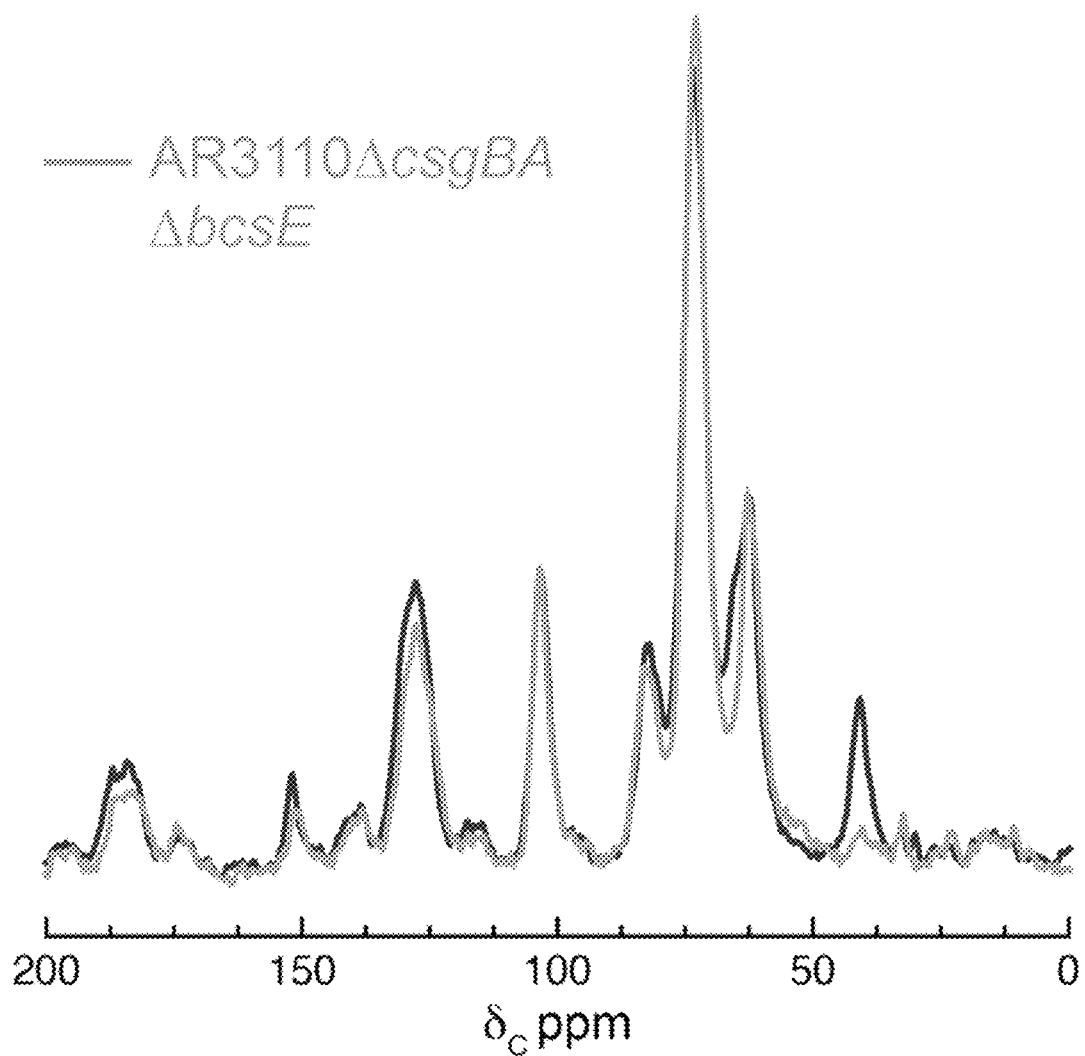
Figure 13C:
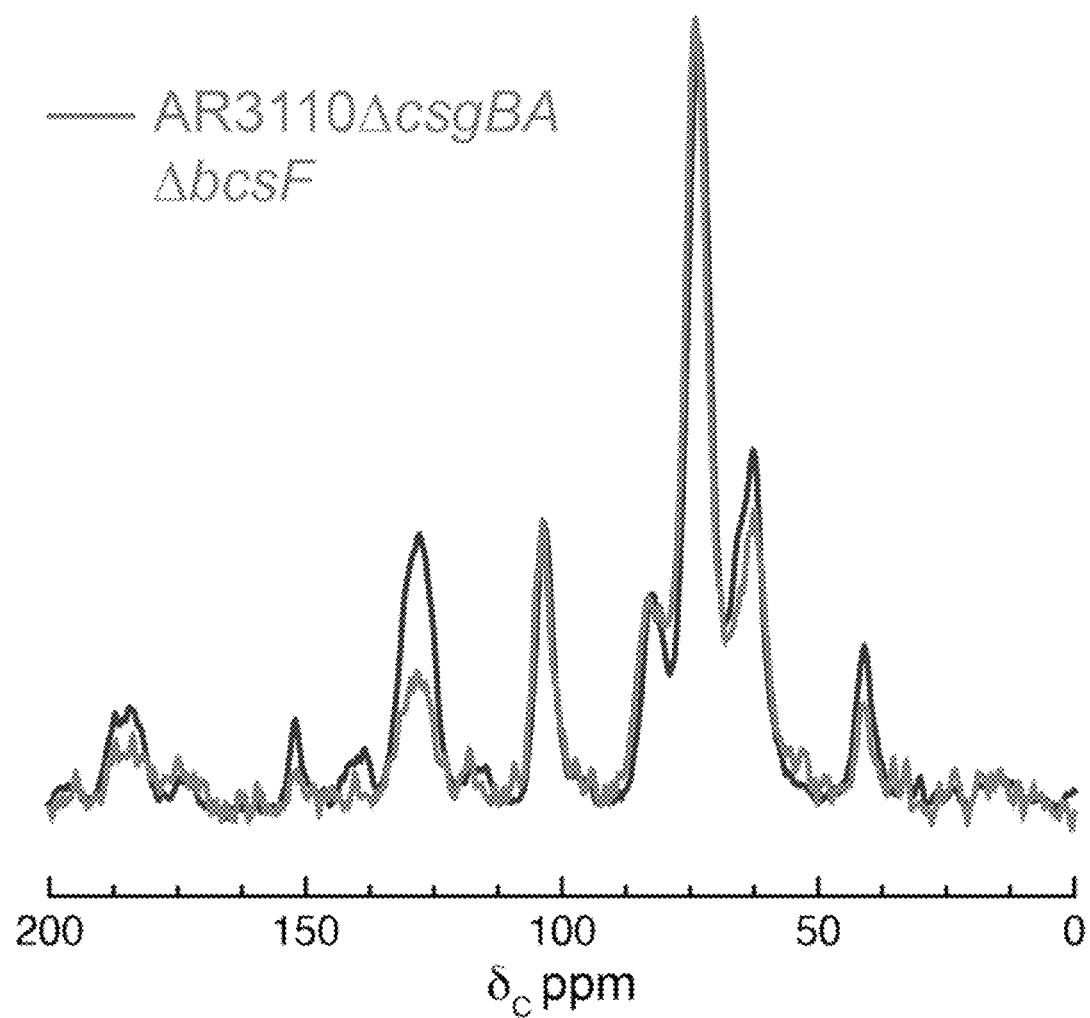
Figure 13D:
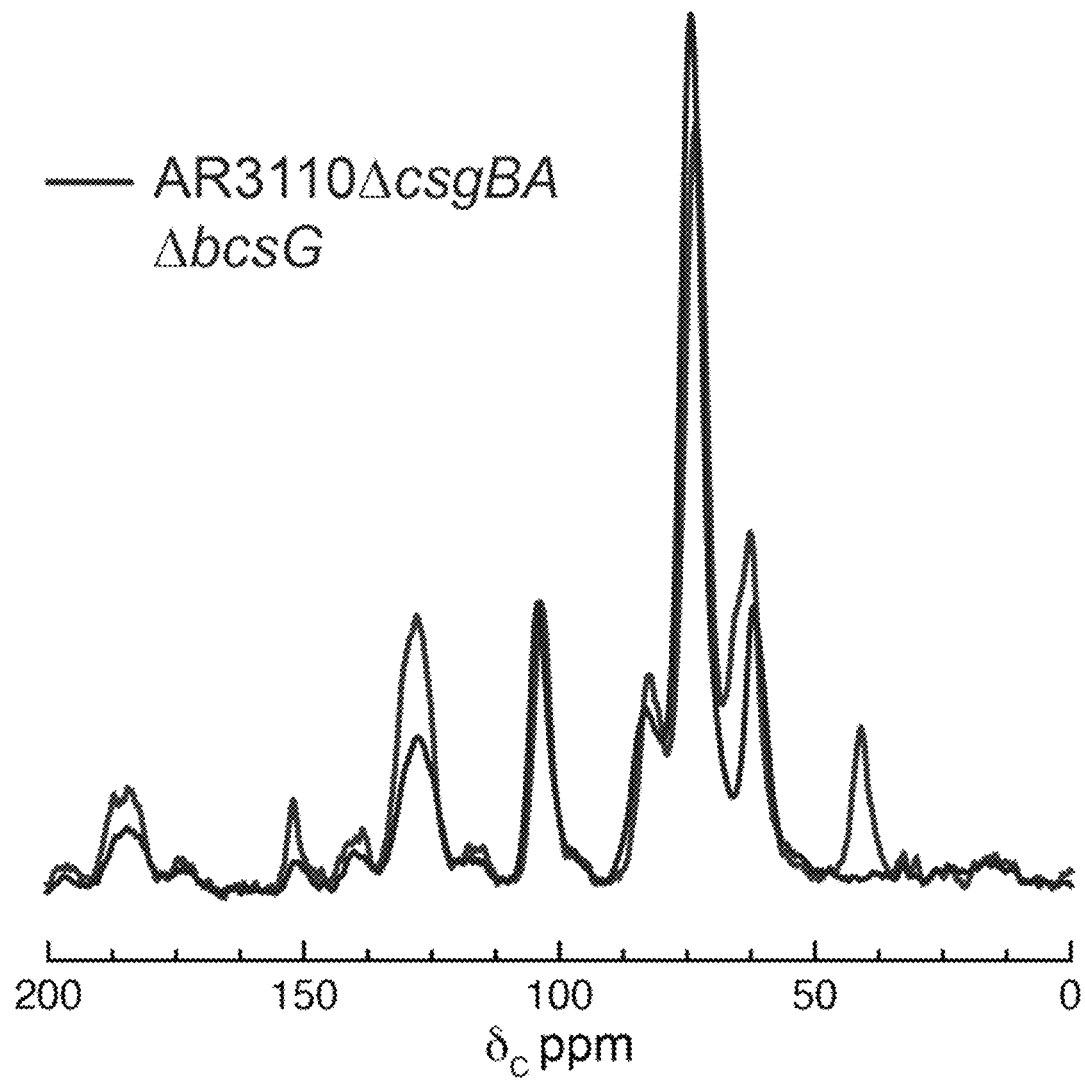

FIG. 12 shows that complementation with bcsG in the AR310ΔcsgBAΔbcsG derivative restores the modification to pEtN cellulose. A 125-MHz $^{13}$C CPMAS NMR spectral comparison revealed that complementation of bcsG in the AR3110AcsgBAΔbcsG derivative restored the phosphoethanolamine modification to the same extent as present in AR3110ΔcsgBA. Cellulosic material was prepared from bacteria grown on CR-supplemented agar as in FIG. 1B. Magic-angle spinning was performed at 7143 Hz.

FIGS. 13A-13D show that the bcsE and bcsF genes contribute to the extent of modification of pEtN cellulose. Cellulosic material was prepared from AR3110ΔcsgBAΔbcsE (FIG. 13B) and AR3110ΔcsgBAΔbcsF (FIG. 13C) grown on CR-supplemented agar as in FIG. 1B. Results were compared with AR3110ΔcsgBA (FIG. 13A) and AR3110ΔcsgBAΔbcsG (FIG. 13D) from FIG. 1. Magic-angle spinning was performed at 7143 Hz.

Figure 14:
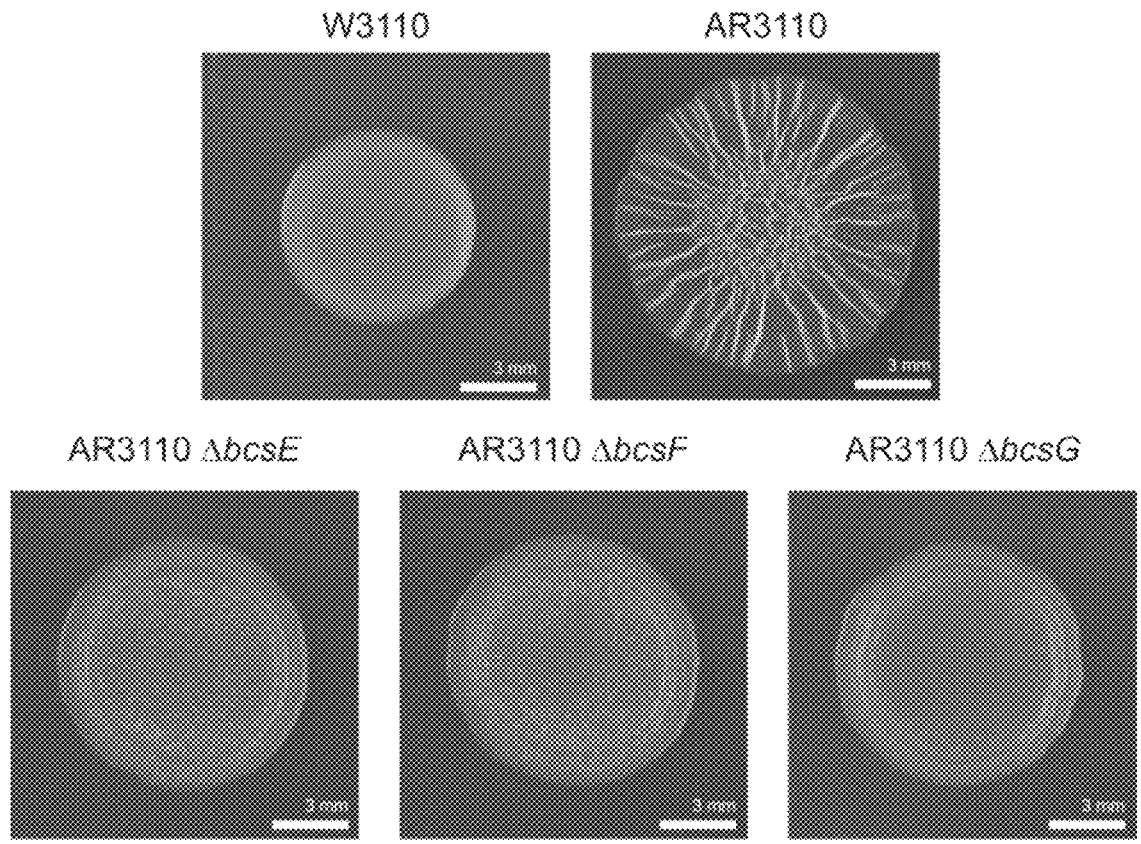

FIG. 14 shows that mutations in bcsE, bcsF and bcsG affect macroscopic morphology of macrocolonies. Macrocolonies of the cellulose-free strain W3110 strain and AR3110, which produces both cellulose and curli fibers and their indicated bcsE, bcsF and bcsG derivatives were grown for 48 hours on YESCA agar plates.

Figure 15:
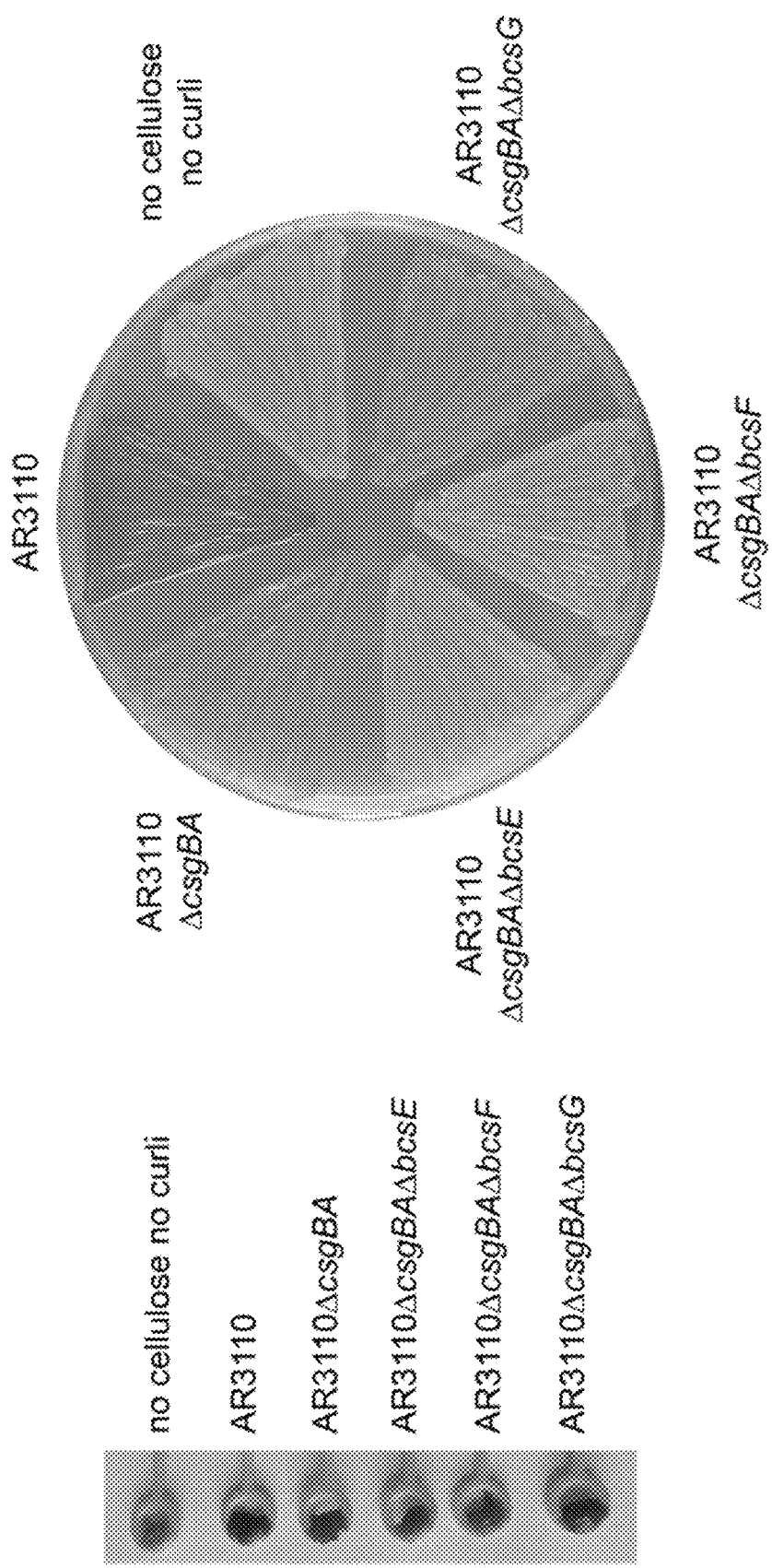

FIG. 15 shows the production of unmodified cellulose by *E. coli* lacking the csgG gene. The AR310ΔcsgBAΔbcsG mutant made significant quantities of unmodified cellulose when cells were grown on nutrient agar medium. Congo red served as an indicator of cellulose production.

Figure 16:
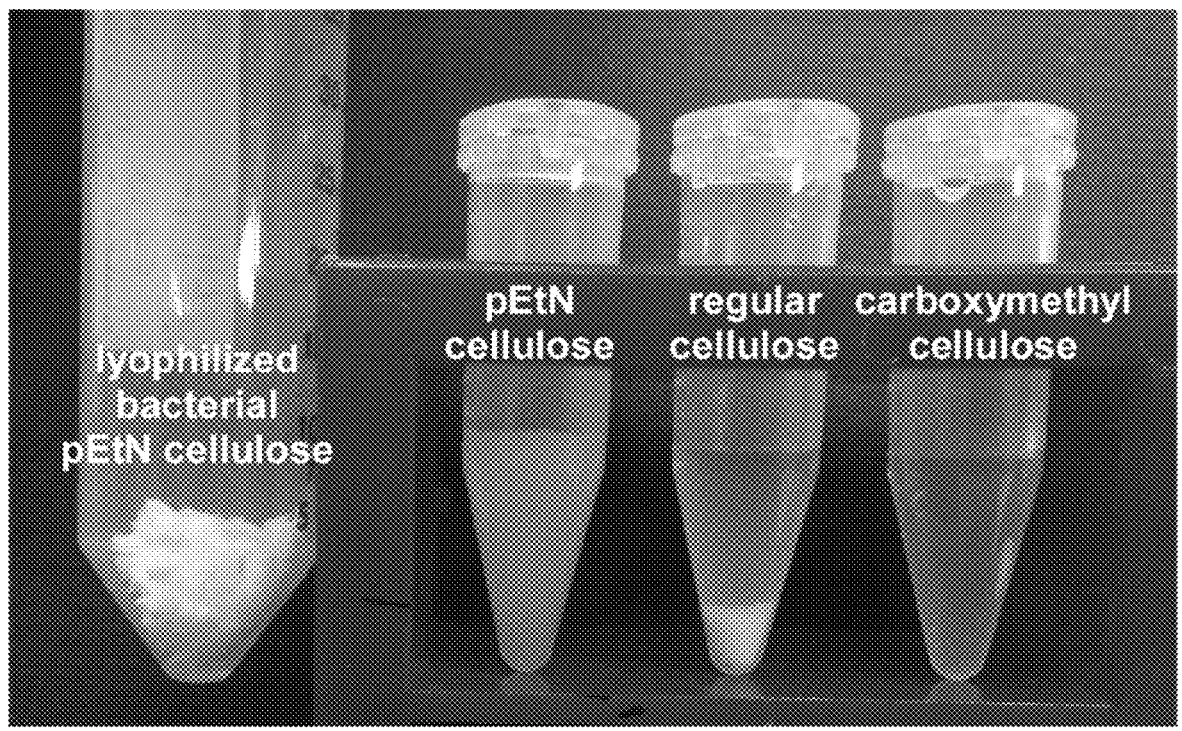

FIG. 16 shows the solubility of phosphoethanolamine cellulose in water. The solubility of purified phosphoethanolamine from *E. coli* was compared with commercially available crystalline cellulose and commercially available carboxymethyl cellulose (produced chemically), the latter known to be soluble in water and highly digestible by cellulases.

Figure 17:
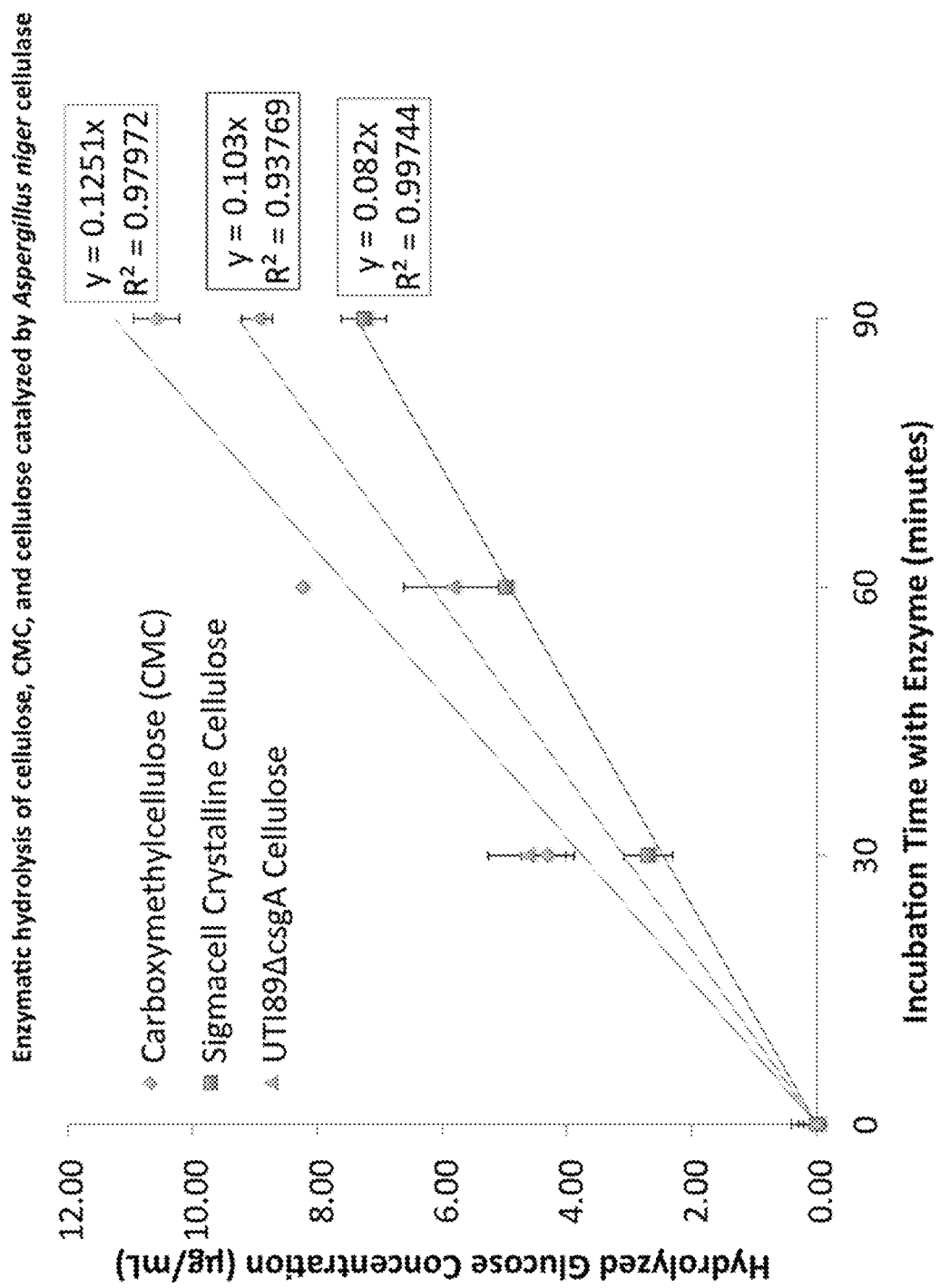

FIG. 17 shows that that phosphoethanolamine cellulose, produced by *E. coli*, is more digestible by cellulase than commercial crystalline cellulose. *Aspergillus niger* cellulase was used for enzymatic hydrolysis of phosphoethanolamine cellulose, crystalline cellulose, and commercially available carboxymethyl cellulose. Glucose was detected with a standard hexokinase assay.

Figure 18:
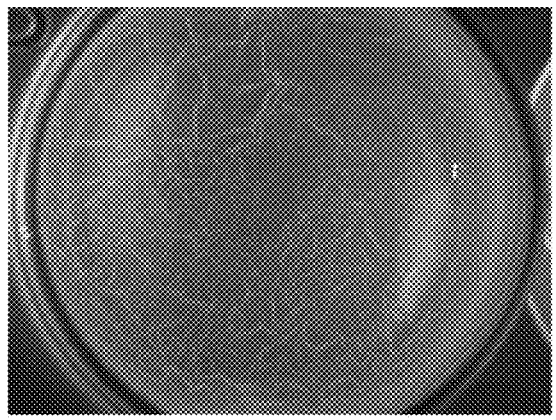
Figure 18:
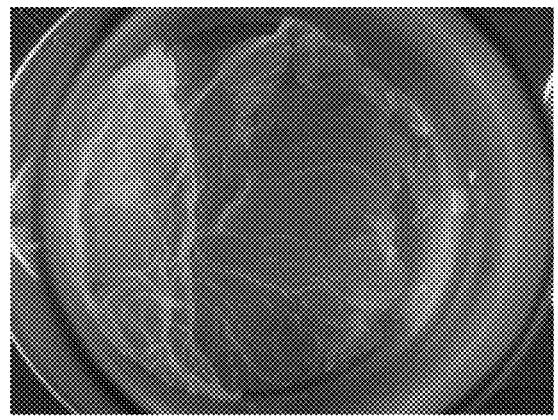

FIG. 18 shows a bacterial biofilm pellicle assay of wild-type and bcsG mutant cells. The normal wild-type *E. coli* extracellular matrix (ECM), which contains the modified pEtN cellulose and curli allows an overall hydrophobic material composed of cells and the ECM to assemble and be maintained at the air liquid interface. This function is lost without the pEtN modification. The bcsG mutant cellulose (unmodified) with curli is different. Although the bcsG mutant forms a type of mesh, it sinks to the bottom of the dish and does not provide a strong network. Thus, the modified cellulose is able to promote the formation of a more hydrophobic material at the air-liquid interface (hydrophobic-hydrophilic interface).

DETAILED DESCRIPTION

The practice of the present invention will employ, unless otherwise indicated, conventional methods of chemistry, biology, biochemistry, and molecular biology and recombinant DNA techniques within the skill of the art. Such techniques are explained fully in the literature. See, e.g., J. Wertz, J. P. Mercier, and O. Bedue *Cellulose Science and Technology* (Fundamental Sciences: Chemistry, EPFL Press, 2010); T. Wuestenberg *Cellulose and Cellulose Derivatives in the Food Industry: Fundamentals and Applications* (Wiley-VCH, 2014); Lehninger, Biochemistry (Worth Publishers, Inc., current addition); Sambrook, et al., *Molecular Cloning: A Laboratory Manual* (3$^{rd}$ Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

I. DEFINITIONS

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a cell" includes two or more cells, and the like.

The term "about," particularly in reference to a given quantity, is meant to encompass deviations of plus or minus five percent.

The terms "polypeptide" and "protein" refer to a polymer of amino acid residues and are not limited to a minimum length. Thus, peptides, oligopeptides, dimers, multimers, and the like, are included within the definition. Both full length proteins and fragments thereof are encompassed by the definition. The terms also include postexpression modifications of the polypeptide, for example, glycosylation, acetylation, phosphorylation, hydroxylation, and the like. Furthermore, for purposes of the present invention, a "polypeptide" refers to a protein which includes modifications, such as deletions, additions and substitutions to the native sequence, so long as the protein maintains the desired activity. These modifications may be deliberate, as through site directed mutagenesis, or may be accidental, such as through mutations of hosts which produce the proteins or errors due to PCR amplification.

The term "BcsG phosphoethanolamine transferase" as used herein encompasses BcsG encoded phosphoethanolamine transferases from any bacterial species, and also includes biologically active fragments, variants, analogs, and derivatives thereof that retain BcsG phosphoethanolamine transferase activity (i.e., catalyze transfer of a phosphoethanolamine group to a cellulose hydroxyl group to produce a phosphoethanolamine-modified cellulose).

A BcsG polynucleotide, nucleic acid, oligonucleotide, protein, polypeptide, or peptide refers to a molecule derived from any source. The molecule need not be physically derived from an organism, but may be synthetically or recombinantly produced. BcsG sequences from a number of bacterial species are well known in the art. Representative sequences are presented for BcsG from *Escherichia coli* (SEQ ID NO:12) and *Salmonella enterica* (SEQ ID NO:13), and additional representative sequences are listed in the National Center for Biotechnology Information (NCBI)

database. See, for example, NCBI entries: NP_417995, NC_000913, YP_002414689, WP_049093031, WP_049185400, WP_049125481, WP_049016646, WP_032425312, WP_057517249, WP_054376814, WP_050272434, WP_050967202, WP_050950257, WP_020978599, WP_020937258, WP_000192030, WP_001541082, WP_088744589, WP_085416812, WP_085347572, WP_052994086, WP_052992671, WP_052992608, WP_052982079, WP_052973396, YP_001008219, YP_206845, NP_744776, WP_048206881, WP_023291299, WP_060082415, WP_049591480, WP_049325226, WP_049300323, WP_049267920, and WP_049217448; all of which sequences (as entered by the date of filing of this application) are herein incorporated by reference. Any of these sequences or a variant thereof comprising a sequence having at least about 70-100% sequence identity thereto, including any percent identity within this range, such as 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity thereto, can be used for cellulose modification, as described herein, wherein the variant retains biological activity, such as BcsG phosphoethanolamine transferase activity.

By "fragment" is intended a molecule consisting of only a part of the intact full-length sequence and structure. The fragment can include a C-terminal deletion an N-terminal deletion, and/or an internal deletion of the polypeptide. Active fragments of a particular protein or polypeptide will generally include at least about 5-10 contiguous amino acid residues of the full length molecule, preferably at least about 15-25 contiguous amino acid residues of the full length molecule, and most preferably at least about 20-50 or more contiguous amino acid residues of the full length molecule, or any integer between 5 amino acids and the full length sequence, provided that the fragment in question retains biological activity, such as BcsG phosphoethanolamine transferase activity.

"Substantially purified" generally refers to isolation of a substance (compound, cellulose or modified cellulose, oligosaccharide, monosaccharide, disaccharide, polysaccharide, polynucleotide, nucleic acid, protein, polypeptide, or peptide) such that the substance comprises the majority percent of the sample in which it resides. Typically in a sample, a substantially purified component comprises 50%, preferably 80%-85%, more preferably 90-95% of the sample. Techniques for purifying cellulose, saccharides, polynucleotides, and polypeptides of interest are well-known in the art and include, for example, ion-exchange chromatography, affinity chromatography and sedimentation according to density.

By "isolated" is meant, when referring to a cellulose or modified cellulose, oligosaccharide, monosaccharide, disaccharide, polysaccharide, or polypeptide, that the indicated molecule is separate and discrete from the whole organism with which the molecule is found in nature or is present in the substantial absence of other biological macromolecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3'P5' phosphoramidates, 2'-O-alkyl-substituted RNA, double- and single-stranded DNA, as well as double- and single-stranded RNA, microRNA, DNA:RNA hybrids, and hybrids between PNAs and DNA or RNA, and also include known types of modifications, for example, labels which are known in the art, methylation, "caps," substitution of one or more of the naturally occurring nucleotides with an analog (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, 0(6)-methylguanine, and 2-thiocytidine), internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. The term also includes locked nucleic acids (e.g., comprising a ribonucleotide that has a methylene bridge between the 2-oxygen atom and the 4'-carbon atom). See, for example, Kurreck et al. (2002) Nucleic Acids Res. 30: 1911-1918; Elayadi et al. (2001) Curr. Opinion Invest. Drugs 2: 558-561; Orum et al. (2001) Curr. Opinion Mol. Ther. 3: 239-243; Koshkin et al. (1998) Tetrahedron 54: 3607-3630; Obika et al. (1998) Tetrahedron Lett. 39: 5401-5404.

"Homology" refers to the percent identity between two polynucleotide or two polypeptide molecules. Two nucleic acid, or two polypeptide sequences are "substantially homologous" to each other when the sequences exhibit at least about 50% sequence identity, preferably at least about 75% sequence identity, more preferably at least about 80% 85% sequence identity, more preferably at least about 90% sequence identity, and most preferably at least about 95% 98% sequence identity over a defined length of the molecules. As used herein, substantially homologous also refers to sequences showing complete identity to the specified sequence.

In general, "identity" refers to an exact nucleotide to nucleotide or amino acid to amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353 358, National biomedical Research Foundation, Washington, D.C., which adapts the local homology algorithm of Smith and Waterman Advances in Appl. Math. 2:482 489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by =HIGH SCORE; Databases=non-redundant, GenBank+EMBL +DDBJ+ PDB+GenBank CDS translations+Swiss protein+Spupdate+ PIR. Details of these programs are readily available.

Alternatively, homology can be determined by hybridization of polynucleotides under conditions which form stable duplexes between homologous regions, followed by digestion with single stranded specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells", "host cells," "cells", "cell lines," "cell cultures," and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a donor polynucleotide, plasmid, or viral vector construct. In addition to the components of the expression cassette, the construct may also include, one or more selectable markers, a signal which allows the construct to exist as single stranded DNA (e.g., a M13 origin of replication), at least one multiple cloning site, and a "mammalian" origin of replication (e.g., a SV40 or adenovirus origin of replication).

"Purified polynucleotide" refers to a polynucleotide of interest or fragment thereof which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (2001) Molecular Cloning, a laboratory manual, 3rd edition, Cold Spring Harbor Laboratories, New York, Davis et al. (1995) Basic Methods in Molecular Biology, 2nd edition, McGraw-Hill, and Chu et al. (1981) Gene 13:197. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as plasmid and viral vectors.

The terms "variant," "analog" and "mutein" refer to biologically active derivatives of the reference molecule that retain desired activity, such as site-directed BcsG phosphoethanolamine transferase activity. In general, the terms "variant" and "analog" refer to compounds having a native polypeptide sequence and structure with one or more amino acid additions, substitutions (generally conservative in nature) and/or deletions, relative to the native molecule, so long as the modifications do not destroy biological activity and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and U.S. Pat. No. 5,977,301; Nguyen et al., Chem. Biol. (2000) 7:463-473; and Simon et al., Proc. Natl. Acad. Sci. USA (1992) 89:9367-9371 for descriptions of peptoids). Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, and tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, adenoviruses, retroviruses, alphaviruses, pox viruses, and vaccinia viruses.

The term "derived from" is used herein to identify the original source of a molecule but is not meant to limit the method by which the molecule is made which can be, for example, by chemical synthesis or recombinant means.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of phosphoethanolamine cellulose and the genetic and molecular basis for its production in bacteria. The bcsEFG operon is part of a cellulose gene cluster implicated in cellulose biosynthesis in *E. coli* and other Gram-negative bacteria. In particular, the inventors have shown that the phosphoethanolamine modification of cellulose depends on a phosphoethanolamine transferase encoded by the BcsG gene. BcsE and BcsF play accessory and possibly regulatory roles, their presence increasing the extent of cellulose modification and the amount of modified cellulose produced (see Examples). The invention further relates to the production, derivatization, and methods of using phosphoethanolamine cellulose.

A. Production of Phosphoethanolamine Cellulose

Phosphoethanolamine cellulose can be prepared in any suitable manner (e.g., biosynthetically, purification from cell culture, or chemical synthesis, etc.). In one embodiment, phosphoethanolamine cellulose is produced biosynthetically by expression of BcsG phosphoethanolamine transferase in a cellulose-producing host, wherein the expressed BcsG phosphoethanolamine transferase catalyzes phosphoethanolamine transfer to hydroxyl groups on cellulose produced by the host. In some embodiments, BcsG is coexpressed with BcsE and BcsF to increase the extent of cellulose modification and/or amount of cellulose production in the host. The amount of phosphoethanolamine cellulose produced may be further increased by providing cyclic di-GMP to upregulate cellulose production in the host. Phosphoethanolamine cellulose, produced by the methods described herein, can be recovered from host cells and further purified if desired. Phosphoethanolamine cellulose is preferably prepared in substantially pure form (i.e. substantially free from other host cell components and other contaminants).

Suitable hosts for production of phosphoethanolamine cellulose include bacteria, plants, and algae, or any other type of organism or cell capable of producing cellulose that can be modified by the BcsG phosphoethanolamine transferase. In some embodiments, phosphoethanolamine cellulose is produced biosynthetically by Gram-negative bacteria, such as, but not limited to, bacteria of the *Acetobacter* (e.g., *Acetobacter xylinum*), *Agrobacterium*, *Escherichia* (e.g., *Escherichia coli*), or *Salmonella* (e.g., *Salmonella enterica*) genuses.

Any BcsG phosphoethanolamine transferase from any bacterial species, or a biologically active fragment, variant, analog, or derivative thereof that retains BcsG phosphoethanolamine transferase activity (i.e., catalyzes transfer of a phosphoethanolamine group to a cellulose hydroxyl group) may be used to produce a phosphoethanolamine-modified cellulose. The BcsG phosphoethanolamine transferase need not be physically derived from an organism, but may be synthetically or recombinantly produced. Representative sequences are presented for BcsG from *Escherichia coli* (SEQ ID NO:12) and *Salmonella enterica* (SEQ ID NO:13), and additional representative sequences are listed in the National Center for Biotechnology Information (NCBI) database. See, for example, NCBI entries: NP_417995, NC_000913, YP_002414689, WP_049093031, WP_049185400, WP_049125481, WP_049016646, WP_032425312, WP_057517249, WP_054376814, WP_050272434, WP_050967202, WP_050950257, WP_020978599, WP_020937258, WP_000192030, WP_001541082, WP_088744589, WP_085416812, WP_085347572, WP_052994086, WP_052992671, WP_052992608, WP_052982079, WP_052973396, YP_001008219, YP_206845, NP_744776, WP_048206881, WP_023291299, WP_060082415, WP_049591480, WP_049325226, WP_049300323, WP_049267920, and WP_049217448; all of which sequences (as entered by the date of filing of this application) are herein incorporated by reference. Any of these sequences or a variant thereof comprising a sequence having at least about 70-100% sequence identity thereto, including any percent identity within this range, such as 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity thereto, can be used for cellulose modification, as described herein, wherein the variant retains biological activity, such as BcsG phosphoethanolamine transferase activity.

The BcsG phosphoethanolamine transferase, alone or in combination with the BcsE and BcsF-encoded proteins, can be used for modification of cellulose produced by a host. Nucleic acids comprising the BcsG, BcsE, or BcsF genes can be inserted into an expression vector to create an expression cassette capable of producing the encoded proteins in a suitable host cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. For purposes of this application, the terms "expression construct," "expression vector," and "vector," are used interchangeably to demonstrate the application of the invention in a general, illustrative sense, and are not intended to limit the invention. The BcsG, BcsE, and BcsF genes may be provided by a single vector or separate vectors. In one embodiment, the vector comprises a bcsEFG operon.

In certain embodiments, the nucleic acid encoding a polypeptide of interest (e.g., BcsG, BcsE, or BcsF-encoded polypeptide) is under transcriptional control of a promoter. A "promoter" refers to a DNA sequence recognized by the synthetic machinery of the cell, or introduced synthetic machinery, required to initiate the specific transcription of a gene. The term promoter will be used here to refer to a group of transcriptional control modules that are clustered around the initiation site for a bacterial RNA polymerase or eukaryotic RNA polymerase (e.g., RNA polymerase I, II, or III). Typical promoters for bacterial expression include the Tac, RecA, LacZ, pBAD, OXB1-20, OXB1, ctc, gsiB, Pspv, and T7 promoters (see, e.g., Goldstein et al. (1995) Biotechnol. Annu. Rev. 1:105-128). Examples of promoters for expression in plants include the CaMV 35S, Xa27, FMV, opine promoters, plant ubiquitin promoter (Ubi), rice actin 1 promoter (Act-1), maize alcohol dehydrogenase 1 promoter (Adh-1), and various other plant pathogen, synthetic, and native promoters (see, e.g., Liu et al. (2016) Curr. Opin. Biotechnol. 37:36-44, Dey et al. (2015) Planta 242(5):1077-1094, Jeong et al. (2015) J. Integr. Plant Biol. 57(11):913-924, Hernandez-Garcia et al. (2014) Plant Sci. 217-218:109-119). These and other promoters can be obtained from commercially available vectors, using techniques well known in the art. See, e.g., Sambrook et al., supra. Enhancer elements may be used in association with a promoter to increase expression levels of the constructs.

An expression vector for expressing BcsG, BcsE, or BcsF comprises a promoter "operably linked" to a polynucleotide comprising a BcsG, BcsE, or BcsF gene sequence. The phrase "operably linked" or "under transcriptional control" as used herein means that the promoter is in the correct location and orientation in relation to a polynucleotide to control the initiation of transcription by RNA polymerase and expression of the polynucleotide.

Typically, transcription terminator/polyadenylation signals may also be present in the expression construct. Bacterial terminator sequences may include Rho-independent or Rho-dependent transcription terminator sequences. Examples of eukaryotic terminator sequences include, but are not limited to, those derived from SV40, as described in Sambrook et al., supra, bovine growth hormone terminator sequence (see, e.g., U.S. Pat. No. 5,122,458), and plant terminator sequences such as the *Agrobacterium* nopaline synthase (NOS) terminator (see, e.g., International Patent Application Publication No. WO 2013/012729, Chung et al. (2005) Trends Plant Sci. 10(8):357-361). Additionally, 5'-UTR sequences can be placed adjacent to the coding sequence in order to enhance expression of the same. Such sequences may include UTRs comprising an internal ribosome entry site (IRES). Inclusion of an IRES permits the translation of one or more open reading frames from a vector. The IRES element attracts a eukaryotic ribosomal translation initiation complex and promotes translation initiation. See, e.g., Kaufman et al., *Nuc. Acids Res.* (1991) 19:4485-4490; Gurtu et al., *Biochem. Biophys. Res. Comm.* (1996) 229:295-298; Rees et al., *BioTechniques* (1996) 20:102-110; Kobayashi et al., *BioTechniques* (1996) 21:399-402; and Mosser et al., BioTechniques (1997 22 150-161.

A multitude of IRES sequences are known and include sequences derived from a wide variety of viruses, such as from leader sequences of picornaviruses such as the encephalomyocarditis virus (EMCV) UTR (Jang et al. *J. Virol.* (1989) 6:1651-1660), the polio leader sequence, the hepatitis A virus leader, the hepatitis C virus IRES, human rhinovirus type 2 IRES (Dobrikova et al., *Proc. Natl. Acad. Sci.* (2003) 100(25):15125-15130), an IRES element from the foot and mouth disease virus (Ramesh et al., *Nucl. Acid Res.* (1996) 24:2697-2700), a giardiavirus IRES (Garlapati et al., *J. Biol. Chem.* (2004) 279(5):3389-3397), and the like. A variety of nonviral IRES sequences will also find use herein, including, but not limited to IRES sequences from yeast, as well as the human angiotensin II type 1 receptor IRES (Martin et al., *Mol. Cell Endocrinol.* (2003) 212:51-61), fibroblast growth factor IRESs (FGF-1 IRES and FGF-2 IRES, Martineau et al. (2004) *Mol. Cell. Biol.* 24(17):7622-7635), vascular endothelial growth factor IRES (Baranick et al. (2008) *Proc. Natl. Acad. Sci. U.S.A.* 105(12):4733-4738, Stein et al. (1998) *Mol. Cell. Biol.* 18(6):3112-3119, Bert et al. (2006) *RNA* 12(6):1074-1083), and insulin-like growth factor 2 IRES (Pedersen et al. (2002) *Biochem. J.* 363(Pt 1):37-44). These elements are readily commercially available in plasmids sold, e.g., by Clontech (Mountain View, Calif.), Invivogen (San Diego, Calif.), Addgene (Cambridge, Mass.) and GeneCopoeia (Rockville, Md.). See also IRESite: The database of experimentally verified IRES structures (iresite.org). An IRES sequence may be included in a vector, for example, to express BcsG in combination with BcsE and BcsF from an expression cassette.

Alternatively, a polynucleotide encoding a viral T2A peptide can be used to allow production of multiple protein products (e.g., BcsG, in combination with BcsE and BcsF) from a single vector. 2A linker peptides are inserted between the coding sequences in the multicistronic construct. The 2A peptide, which is self-cleaving, allows co-expressed proteins from the multicistronic construct to be produced at equimolar levels. 2A peptides from various viruses may be used, including, but not limited to 2A peptides derived from the foot-and-mouth disease virus, equine rhinitis A virus, Thosea asigna virus and porcine teschovirus-1. See, e.g., Kim et al. (2011) *PLoS One* 6(4):e18556, Trichas et al. (2008) *BMC Biol.* 6:40, Provost et al. (2007) *Genesis* 45(10):625-629, Furler et al. (2001) *Gene Ther.* 8(11):864-873; herein incorporated by reference in their entireties.

One of skill in the art can readily determine BcsG, BcsE, and BcsF nucleotide sequences using standard methodology and the teachings herein. Oligonucleotide probes can be devised based on the known sequences and used to probe genomic or cDNA libraries. The sequences can then be further isolated using standard techniques and, e.g., restriction enzymes employed to truncate the gene at desired portions of the full-length sequence. Similarly, sequences of interest can be isolated directly from cells containing the same, using known techniques, such as phenol extraction and the sequence further manipulated to produce the desired truncations. See, e.g., Sambrook et al., supra, for a description of techniques used to obtain and isolate DNA.

The BcsG, BcsE, and BcsF sequences can also be produced synthetically, for example, based on their known sequences. The nucleotide sequence can be designed with the appropriate codons for the particular amino acid sequence desired. The complete sequence is generally assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311; Stemmer et al. (1995) *Gene* 164:49-53.

Once coding sequences have been isolated and/or synthesized, they can be cloned into any suitable vector or replicon for expression. Numerous expression vectors are known to those of skill in the art, and the selection of an appropriate expression vector is a matter of choice. For example, a bacterial plasmid expression vector may be used to transform a bacterial host. Bacterial expression vectors include, but are not limited to, pACYC177, pASK75, pBAD, pBADM, pBAT, pCal, pET, pETM, pGAT, pGEX, pHAT, pKK223, pMal, pProEx, pQE, and pZA31 vectors. See, e.g., Sambrook et al., supra.

Alternatively, plant expression systems can also be used to produce modified cellulose as described herein. Generally, such systems use virus-based vectors to transfect plant cells with heterologous genes. Exemplary plant viruses include the tobacco mosaic virus (TMV), potato virus X, and cowpea mosaic virus. A number of plant expression systems use the Ti plasmid of *Agrobacterium tumefaciens*. For a description of plant expression systems, see, e.g., Zaidi et al. (2017) *Front. Plant Sci.* 8:539; Hefferon (2014) *Biomed. Res. Int.* 2014:785382; Porta et al. (1996) *Mol. Biotech.* 5:209-221; and Hackland et al. (1994) *Arch. Virol.* 139:1-22. In addition, algae expression systems are available for *Chlamydomonas reinhardtii* and Synechococcus *elongatus*. See, e.g., Doron et al. (2016) *Front. Plant Sci.* 7:505 and Griesbeck et al. (2006) *Mol. Biotechnol.* 34(2):213-223.

A gene can be placed under the control of a promoter, ribosome binding site (for bacterial expression) and, optionally, an operator (collectively referred to herein as "control" elements), so that the DNA sequence encoding the desired polypeptide is transcribed into RNA in the host cell transformed by a vector containing this expression construction. The coding sequence may or may not contain a signal peptide or leader sequence. With the present invention, both the naturally occurring signal peptides and heterologous sequences can be used. Leader sequences can be removed by the host in post-translational processing. See, e.g., U.S. Pat. Nos. 4,431,739; 4,425,437; 4,338,397. Such sequences include, but are not limited to, the TPA leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences. The control sequences and other regulatory sequences may be ligated to the coding sequence prior to insertion into a vector. Alternatively, the coding sequence can be cloned directly into an expression vector that already contains the control sequences and an appropriate restriction site.

In some cases, it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., *supra; DNA Cloning*, Vols. I and II, *supra; Nucleic Acid Hybridization, supra.*

The expression vector is then used to transform an appropriate cellulose-producing host cell. Depending on the expression system and host selected, the modified cellulose is produced by growing host cells transformed by an expression vector described above under conditions whereby the BcsG phosphoethanolamine transferase is expressed (i.e., with or without the BcsE and BcsF-encoded proteins). The BcsG phosphoethanolamine transferase catalyzes phosphoethanolamine transfer to hydroxyl groups of the cellulose produce by the host. The selection of the appropriate growth conditions is within the skill of the art.

Phosphoethanolamine cellulose can be produced in bacteria, for example, by culturing bacteria in media containing a suitable carbon source. Exemplary carbon sources include monosaccharides (e.g., glucose and fructose), disaccharides (e.g., sucrose, maltose, and lactose), oligosaccharides, polysaccharides (e.g., starch hydrolysates), mannitol, ethanol, acetic acid, citric acid, glycerol, beet molasses (B-Mol), and biodiesel fuel by-product (BDF-B). One or more carbon sources may be used. The choice of carbon sources will depend on the type of bacteria used for production of cellulose, the culture conditions, the cost of production, and the like. Media may be supplied manually or automatically with a continuous, batch, or semi-batch fed culture system.

B. Applications

Phosphoethanolamine cellulose will find use in a wide variety of industrial, nutritional, electronic, scientific, and medical applications. For example, phosphoethanolamine cellulose may be used in various applications in which other forms of cellulose are currently used, such as in production of paper, textile, biofuels, food, pharmaceutical fillers, cellulose composites for electronic devices, nanocellulosie materials, and liquid filtration and chromatographic media.

The phosphoethanolamine group enhances solubility of the cellulose and facilitates the conversion of the polymer to shorter polysaccharides and oligosaccharides or monosaccharides such as glucose through physical, chemical (e.g., acid hydrolysis), or enzymatic (e.g., cellulase catalyzed hydrolysis) methods. For example, phosphoethanolamine cellulose can be hydrolyzed by contacting the phosphoethanolamine cellulose with one or more cellulases. In certain embodiments, one or more endocellulases, exocellulases, beta-glucosidases, oxidative cellulases, cellulose phosphorylases, or a combination thereof are used in hydrolysis of phosphoethanolamine cellulose.

The enhanced conversion of phosphoethanolamine cellulose to glucose provides an attractive route for production of ethanol from cellulosic biomass either in bacteria (e.g., *Escherichia coli, Acetobacter xylinum*, or other bacterial cellulose producer) or through bioengineering of other organisms to express bcsG (e.g., either by itself or in combination with the bcsE and bcsF genes), for example, in *Miscanthus* or other plants or algae.

The phosphoethanolamine cellulose may also be further modified due to its reactive amine group functionality to generate a wide number of other cellulosic materials. For example, the amine group is readily alkylated, acylated, or sulfonated. In particular, the amine group can be conjugated to various agents such as peptides, antibodies, enzymes, nucleic acids, dyes, ligands, or drugs. Methods for conjugating amines are well known in the art. For example, conjugation may be performed with amine-reactive succinimidyl esters or click chemistry. For a description of various conjugation techniques, see, e.g., Bioconjugation Protocols: Strategies and Methods (S. S. Mark ed., Humana Press, 2016), G. T. Hermanson Bioconjugate Techniques (Academic Press, 3rd edition, 2013), Click Chemistry for Biotechnology and Materials Science (J. Lahann ed., Wiley, 2009); herein incorporated by reference in their entireties.

In particular, phosphoethanolamine cellulose can be chemically modified to produce useful cellulose ester and ether derivatives. For example, cellulose ester derivatives can be formed by esterification of cellulose hydroxyl groups with an organic acid, acid anhydride, or acid chloride, or an inorganic acid. Exemplary organic acids that can be used in esterification include acetic acid, propanoic acid, and butyric acid. Alternatively, the corresponding acid anhydrides (e.g., acetic anhydride, propionic anhydride, and butyric anhydride) or acid chlorides (e.g., acetyl chloride) can be used. Exemplary inorganic acids that can be used in esterification include nitric acid and sulfuric acid. For a description of methods of synthesizing cellulose esters, see, e.g., Edgar et al. (2001) *Progress in Polymer Science* 26:1605-1688, Cao et al. (2013) *J. Agric. Food Chem.* 61:2489-2495, Heinze et al. (2003) *Cellulose* 10:283-296, Krassig (1993) Cellulose (Polymer Monographs) Volume 11, CRC Press, Liebert et al. (2005) *Biomacromolecules* 6:333-340, El-Sakhawy et al. (2014) *J. Drug Deliv.* 2014:575969, U.S. Pat. Nos. 9,624, 311, 9,458,248, 9,217,043, 9,708,415, 8,273,872, 6,184,373, 5,750,677, 2,651,629, and 3,097,051; herein incorporated by reference. Cellulose esters are commonly used, for example, as binders, coating additives, and film formers or modifiers, and may find use in automotive, wood, plastic, paper, apparel, photography, and leather coatings applications.

Alternatively, the cellulose hydroxyl groups can be chemically modified to produce a cellulose ether, such as an alkyl ether (e.g., methylcellulose, ethylcellulose), hydroxyalkyl ether (e.g., hydroxyethylcellulose, hydroxylpropyl cellulose), or carboxyalkyl ether (e.g., carboxymethylcellulose). Cellulose ethers are commonly prepared using an alkali metal hydroxide to deprotonate cellulose hydroxyl groups, which are reacted with an etherifying agent such as an alkyl halide, alkyl sulfate, alkylene oxide, or chlorohydrin. For a description of methods of synthesizing cellulose ethers, see, e.g., Kristin Schumann et al. (2009) *Macromo-* lecular Symposia 280:86-94, Goncalves et al. (2015) Carbohydrate Polymers 116:51-59, Lorand (1939) Ind. Eng. Chem. 31:891-897, U.S. Pat. Nos. 2,512,338, 8,541,571, and 9,580,516; herein incorporated by reference. Cellulose ethers are commonly used, for example, as thickeners, binders, film formers, water-retention agents, suspension aids, surfactants, lubricants, and protective colloids and emulsifiers, and may find use in construction, ceramics, paints, foods, cosmetics, and pharmaceuticals.

In particular, cellulose esters and ethers may find use in pharmaceuticals for sustained and controlled release formulations, osmotic drug delivery systems, bioadhesives and mucoadhesives, compressibility enhancers in tablets, liquid dosage forms as thickening agents and stabilizers, binders in tablets, semisolid preparations as gelling agents, and various other applications.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Phosphoethanolamine Cellulose: A Naturally Produced Chemically Modified Cellulose

INTRODUCTION

Here, we report on the determination of the structure of a modified cellulose, phosphoethanolamine cellulose (pEtN cellulose), produced naturally by *E. coli* and other Gram-negative bacteria. We provide the genetic basis for its production and the functional implications of gene-directed pEtN cellulose synthesis.

*E. coli* and *Salmonella* are among the best-studied microorganisms reported to produce cellulose. These include human pathogens such as uropathogenic and enterohemorrhagic *E. coli*. Functionally, the exopolysaccharide cellulose is a major component of the self-produced extracellular matrix in biofilms, which represent physiologically heterogeneous and spatially structured bacterial communities (Stewart et al. (2008) *Nature Rev. Microbiol.* 6, 199-210; Serra et al. (2013) mBio 4(2), e00103-00113). Biofilm formation is of high medical relevance as it confers enhanced resistance to antibiotics and host defenses during infection (Anderson et al. (2008) *Curr. Top. Microbiol. Immunol.* 322, 87-107). Within the biofilm matrix, cellulose forms a nanocomposite with amyloid curli fibers that encapsulates individual cells in supramolecular basket-like structures, enmeshes the bacterial community and confers cohesion and elasticity that allows biofilms to fold and buckle up in a tissue-like manner (Hung et al. (2013) mBio 4, e00645-00613; McCrate et al. (2013) *J. Mol. Biol.* 425, 4286-4294; Serra et al. (2013) *J. Bacteriol.* 195, 5540-5554). Biochemical and solid-state NMR measurements with the clinically important uropathogenic *E. coli* strain UTI89 established that the matrix was composed of curli fibers and cellulosic material in a 6:1 ratio by mass. During this bottom-up analysis involving $^{13}$C and $^{15}$N NMR analysis of the purified components, we also discovered that the cellulose portion appeared to be modified in some way with an aminoethyl functionality (McCrate et al., supra).

Figure 3:
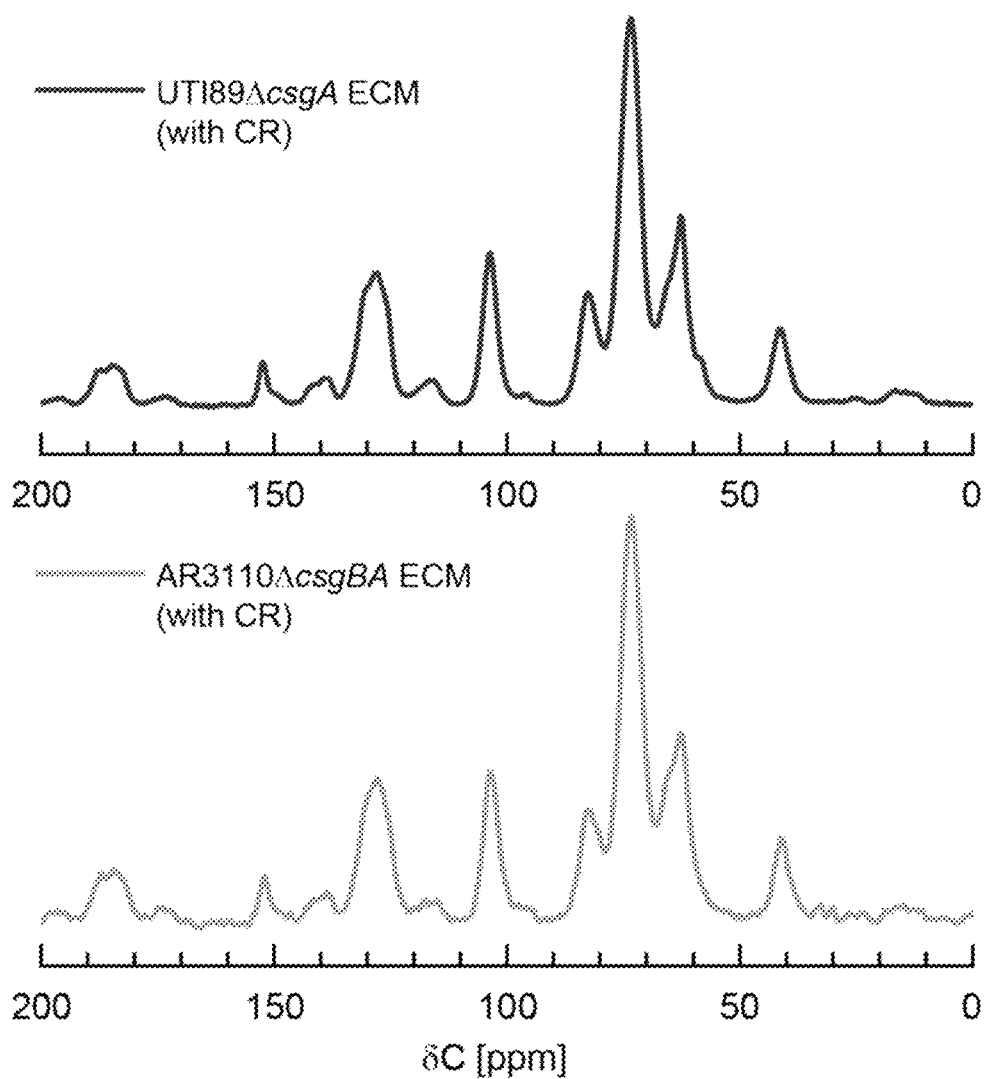
FIG. 3 shows that the phosphoethanolamine cellulose spectrum from AR3110ΔcsgBA is nearly identical to that from the uropathogenic *E. coli* derivative UTI89ΔcsgA. 125-MHz $^{13}$C CPMAS NMR spectra were obtained for the modified cellulose samples obtained from cells grown on CR-supplemented YESCA agar. Magic-angle spinning was performed at 7143 Hz.

Solid-state NMR analysis of the intact cellulosic material, complemented by solution-state NMR analysis of acid-digested material, has now enabled the determination of the chemical structure of the modified cellulose as a polymer containing glucose and glucose-6-phosphoethanolamine (FIG. 1A). The $^{13}$C CPMAS spectrum of cellulose isolated from the laboratory strain of *E. coli*, AR3110ΔcsgB, which lacks amyloid curli fibers, contains carbon contributions from the glucose backbone plus two additional carbons at 41 ppm and 63 ppm (FIG. 1B). The C6 carbon appears at 62 ppm for the unmodified glucose units and at 66 ppm for the modified glucose units. The isolation and purification of the cellulosic polymer from *E. coli* was aided by the use of the classic dye Congo red (Reichhardt et al. (2016) *Anal. Bioanal. Chem.* 408, 7709-7717). Congo red (CR) is commonly used as a supplement in nutrient agar plates for evaluation of *E. coli* and *Salmonella* community phenotypes since both curli and cellulosic polymers bind the dye while generating the hallmark colony wrinkling exhibited by biofilm-producing Enterobacteriaceae (Romling (2005) *Cell. Mol. Life Sci.* 62, 1234-1246). The use of the dye did not alter the modification of cellulose, and the $^{13}$C centerband peaks associated with CR are resolved from cellulose (FIG. 1B). The CR-containing $^{13}$C CPMAS spectrum for the modified cellulose from AR310ΔcsgB is identical to that from the UTI89 curli mutant, UTI89ΔcsgA (FIG. 3).

Figure 4:
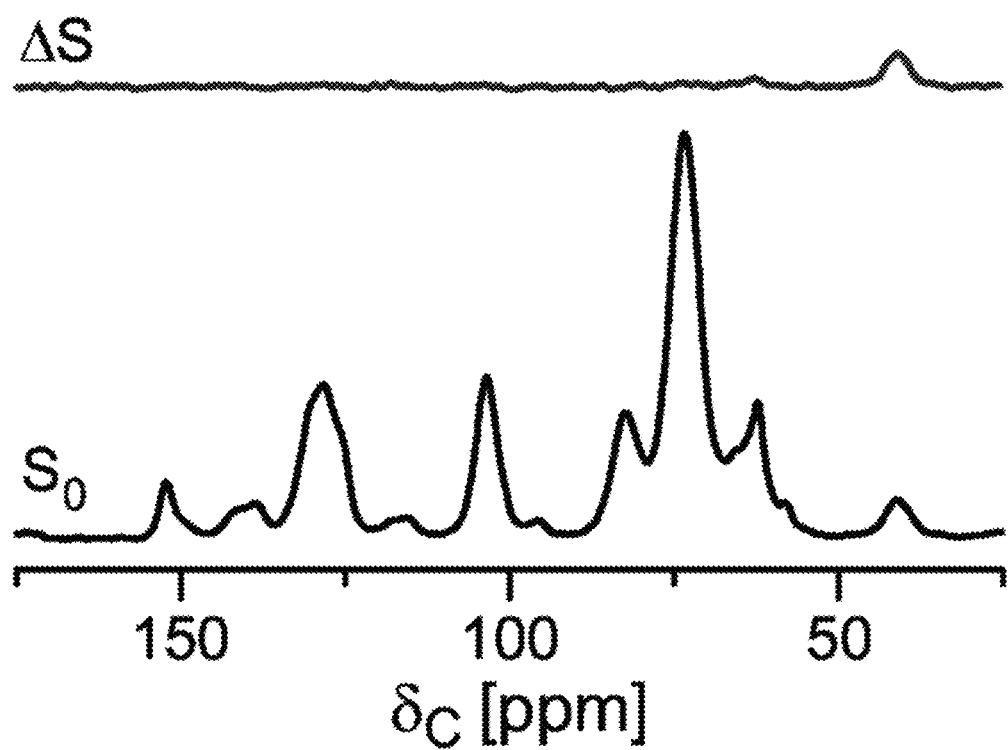
FIG. 4 shows that C{N}REDOR NMR confirmed that the C8 carbon is adjacent to a nitrogen in the AR3110ΔcsgBA modified cellulose. 125-MHz C{N}REDOR was performed with an evolution time of 2.2 ms to identify carbons directly bonded to nitrogen. The REDOR difference (DS) spectrum confirmed that the C8 carbon at 41 ppm exhibited complete dephasing as expected for directly bonded CN pairs. Magic-angle spinning was performed at 7143 Hz.
Figure 5:
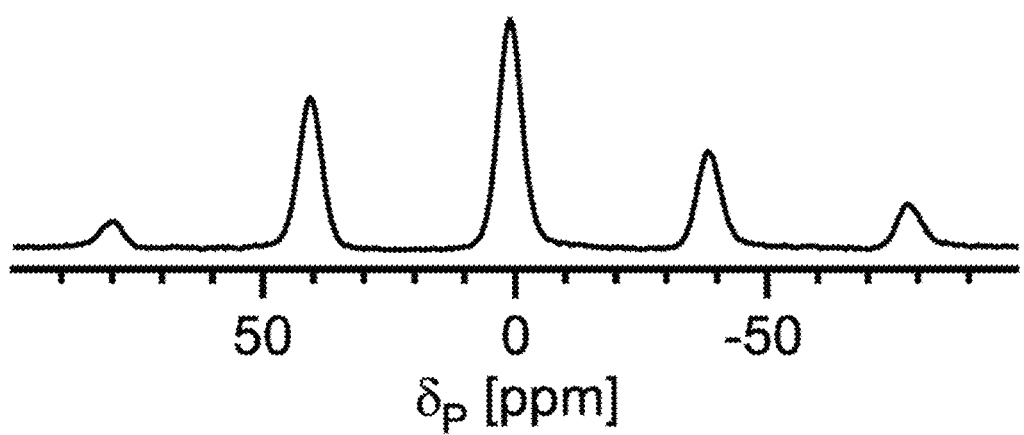
FIG. 5 shows that $^{31}$P CPMAS NMR revealed the presence of phosphorous in the modified cellulose. 202-MHz $^{31}$P CPMAS NMR was performed to identify the presence of phosphorous in the modified cellulose isolated from AR3110ΔcsgBA. The $^{31}$P centerband is centered at 1.2 ppm, referenced to calf thymus DNA, consistent with a phosphate species. Spinning sidebands are observed at multiples of the spinning frequency. Magic-angle spinning was performed at 8000 Hz.
Figure 6A:
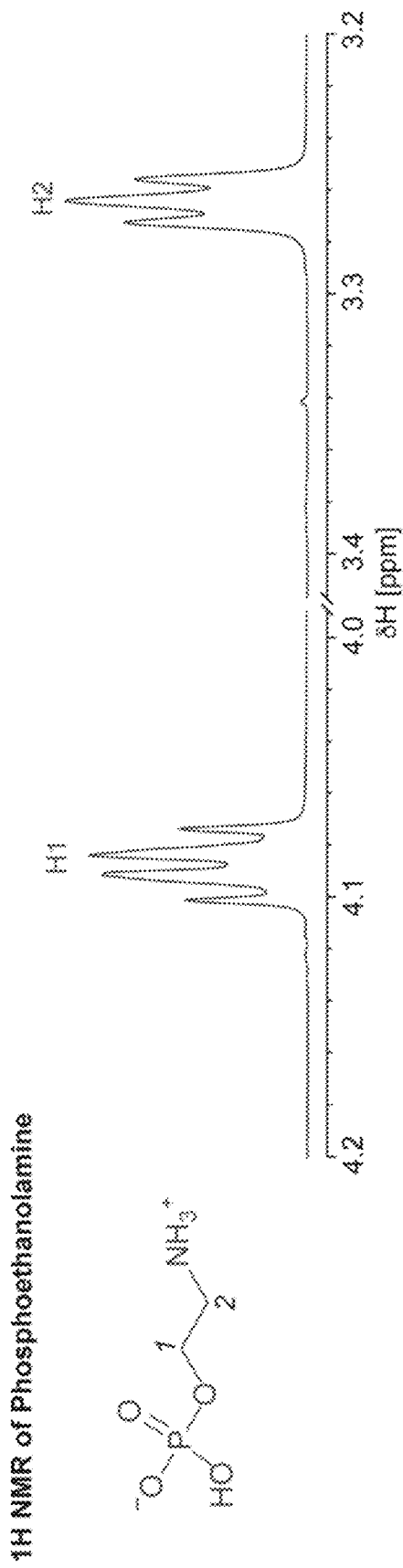
FIGS. 6A and 6B show that solution-state NMR of the intact pEtN cellulose revealed observable $^1$H signals consistent with a phosphoethanolamine modification. $^1$H NMR resonances for the $^1$H's attached to C1 and C2 carbons in pEtN cellulose (FIG. 6B) exhibit the splitting patterns expected for phosphoethanolamine (FIG. 6A). $^1$H NMR was performed at 600 MHz on a Varian solution-state NMR spectrometer.
Figure 6B:
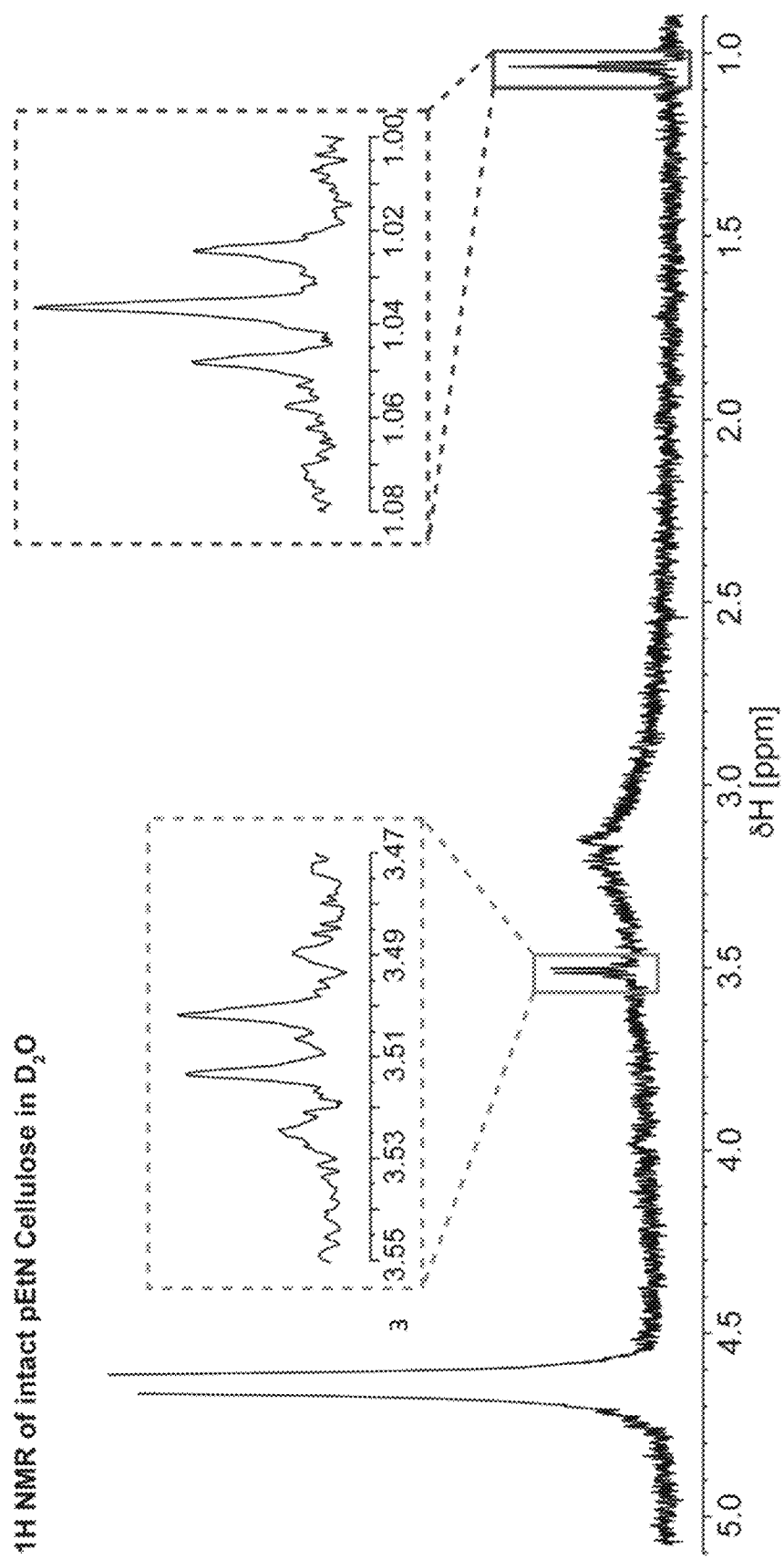
Figure 7A:
FIGS. 7A-7D show solution-state $^{13}$C NMR spectral comparisons assigning the contributions to the acid-digested pEtN cellulose $^{13}$C spectrum. 150-MHz $^{13}$C solution-state NMR spectra of ethanolamine (FIG. 7A), glucose (FIG. 7B), and glucose-6-phosphate (FIG. 7C) were obtained to provide spectral comparisons with acid-digested pEtN cellulose (FIG. 7D). Acid digestion of pEtN cellulose resulted in cleavage of the cellulosic polymer and loss of ethanolamine with carbon signals consistent with glucose-6-phosphate and ethanolamine in solution. Spectra were referenced to DSS.
Figure 7B:
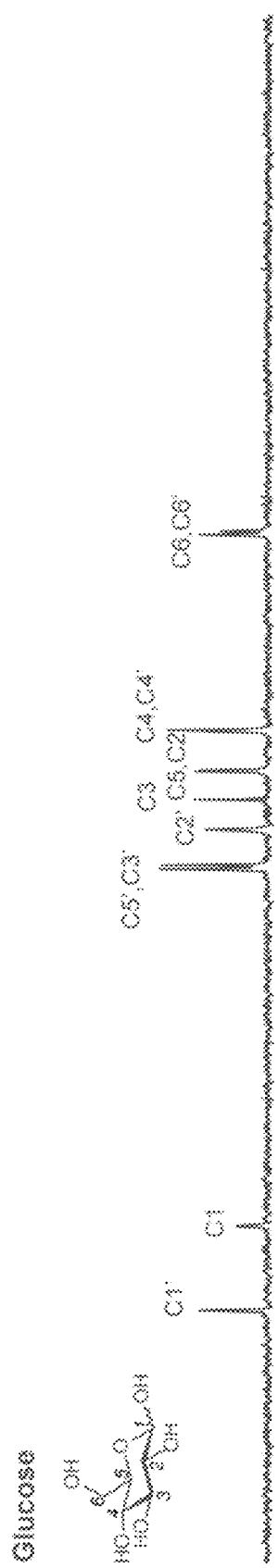
Figure 7C:
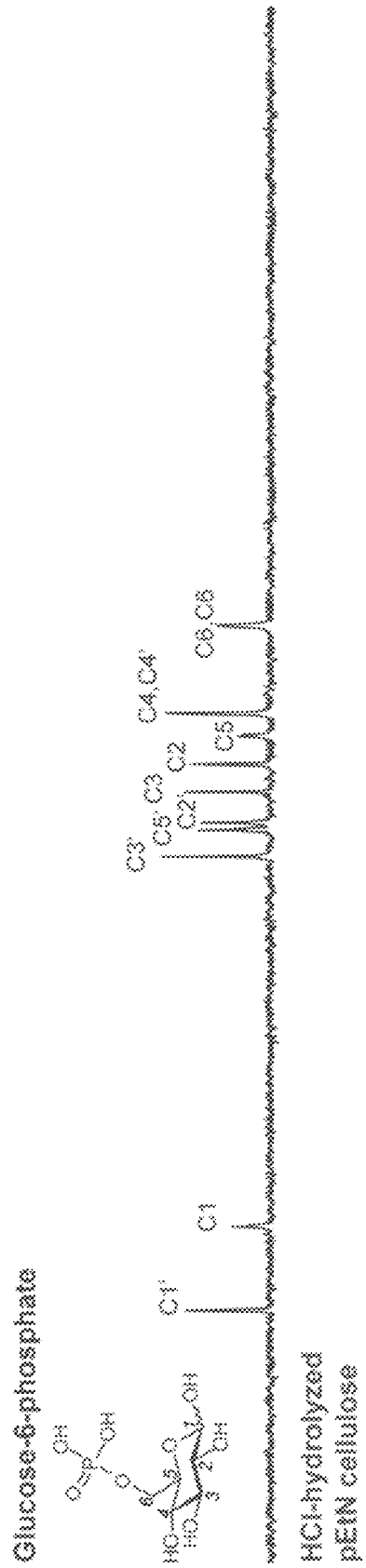
Figure 7D:
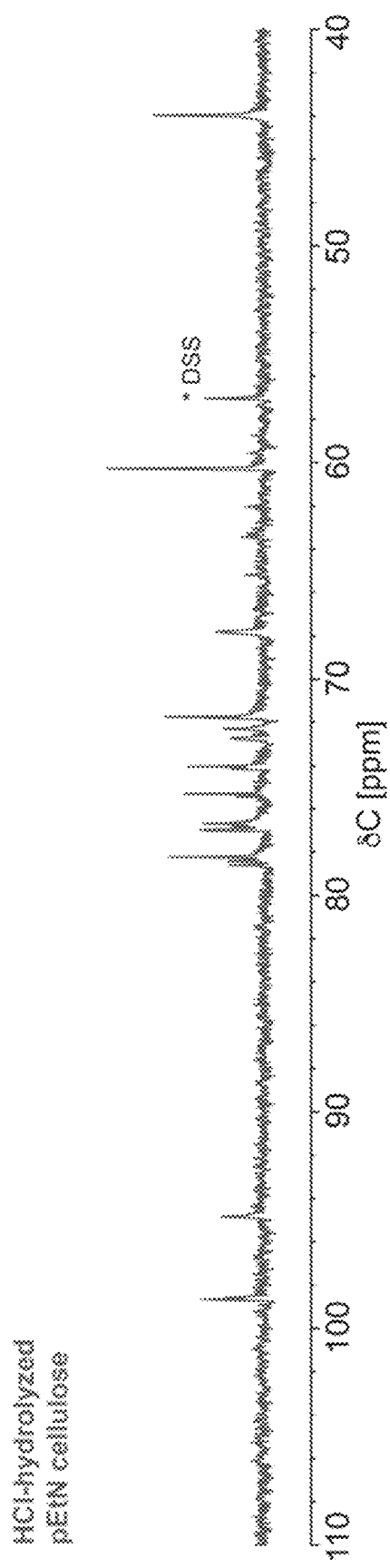
Figure 8A:
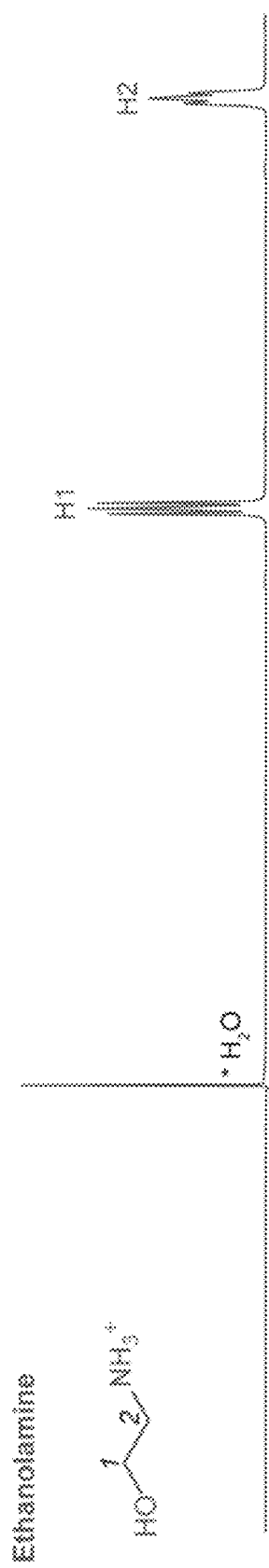
FIGS. 8A-8D show solution-state $^1$H NMR spectral comparisons assigning the dominant contributions to the acid-digested pEtN cellulose $^{13}$C spectrum. 600-MHz $^1$H solution-state NMR spectra of ethanolamine (FIG. 8A), glucose (FIG. 8B), and glucose-6-phosphate (FIG. 8C) were obtained to provide spectral comparisons with acid-digested pEtN cellulose (FIG. 8D). Acid digestion of pEtN cellulose resulted in cleavage of the cellulosic polymer and loss of ethanolamine with carbon signals consistent with glucose-6-phosphate and ethanolamine in solution.
Figure 8B:
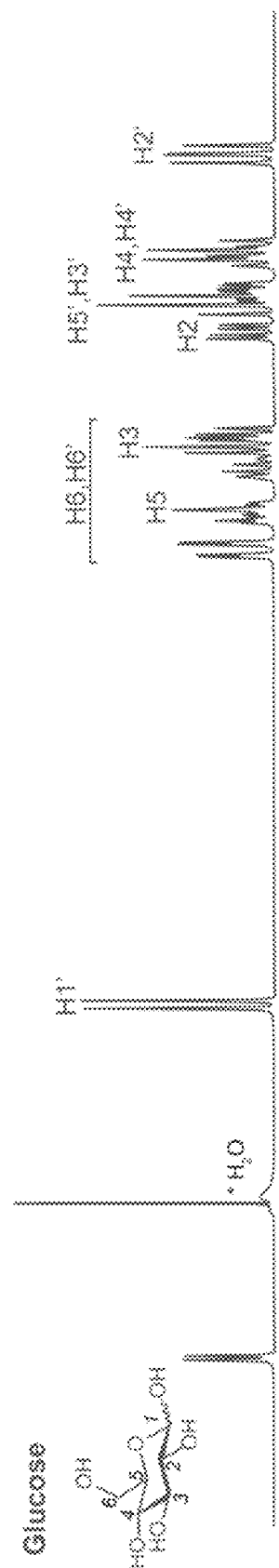
Figure 8C:
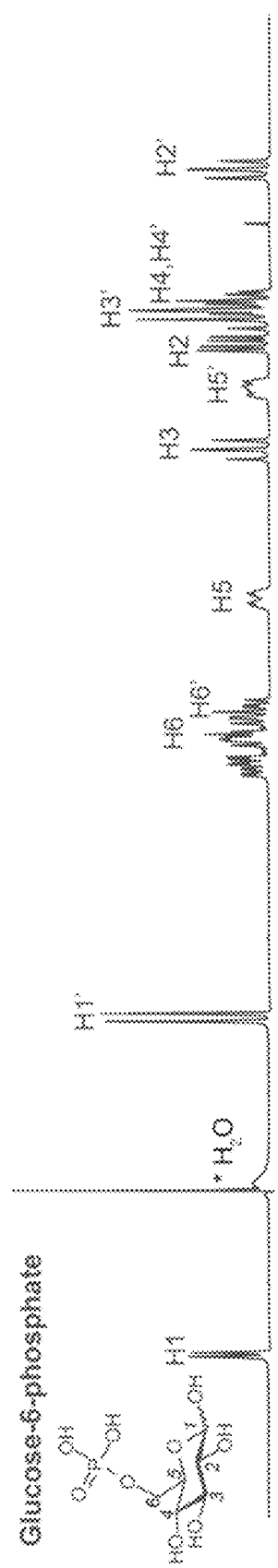
Figure 8D:
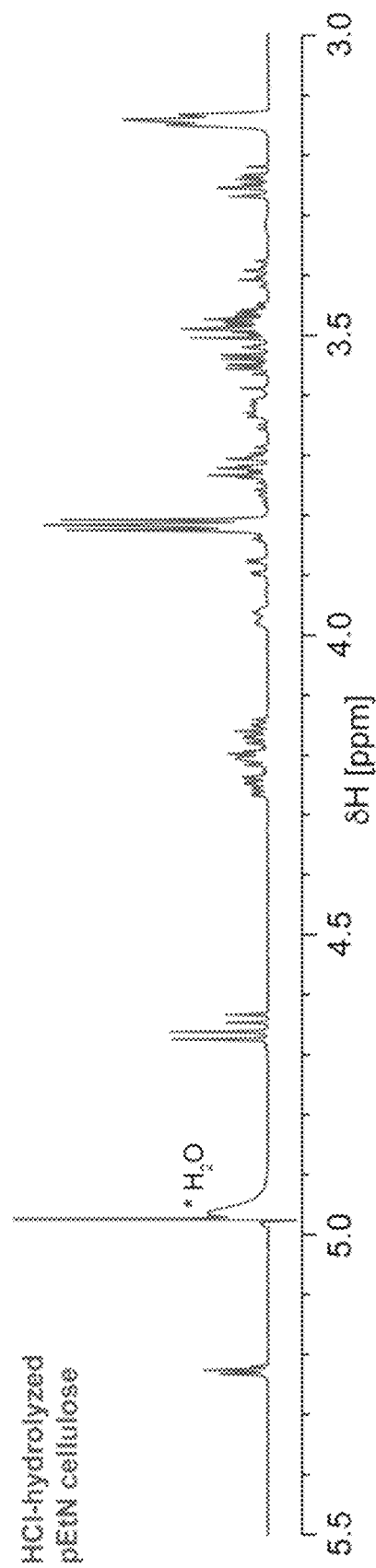

C{N}REDOR assigned the 41-ppm carbon peak as the C8 carbon, the only carbon that is directly bonded to nitrogen (FIG. 4). $^{31}$P CPMAS (FIG. 5) and C{P}REDOR (FIG. 1C) confirmed the presence of $^{31}$P in the polymer and indicated that the full modification is a phosphoethanolamine extending from the C6 carbon, wherein phosphorus is nearest to the C6 and C7 carbons and next closest to the C5 and C8 carbons (FIG. 1B). Solution-state NMR analysis of the intact cellulose would ordinarily not be expected to reveal resolved carbons given the insolubility of the material. Yet, the sufficient mobility of the *E. coli* modified cellulose enabled the detection of $^1$H resonances with splitting patterns resembling those of —OCH2- and —CH2N— in phosphoethanolamine (FIG. 6).

Figure 9:
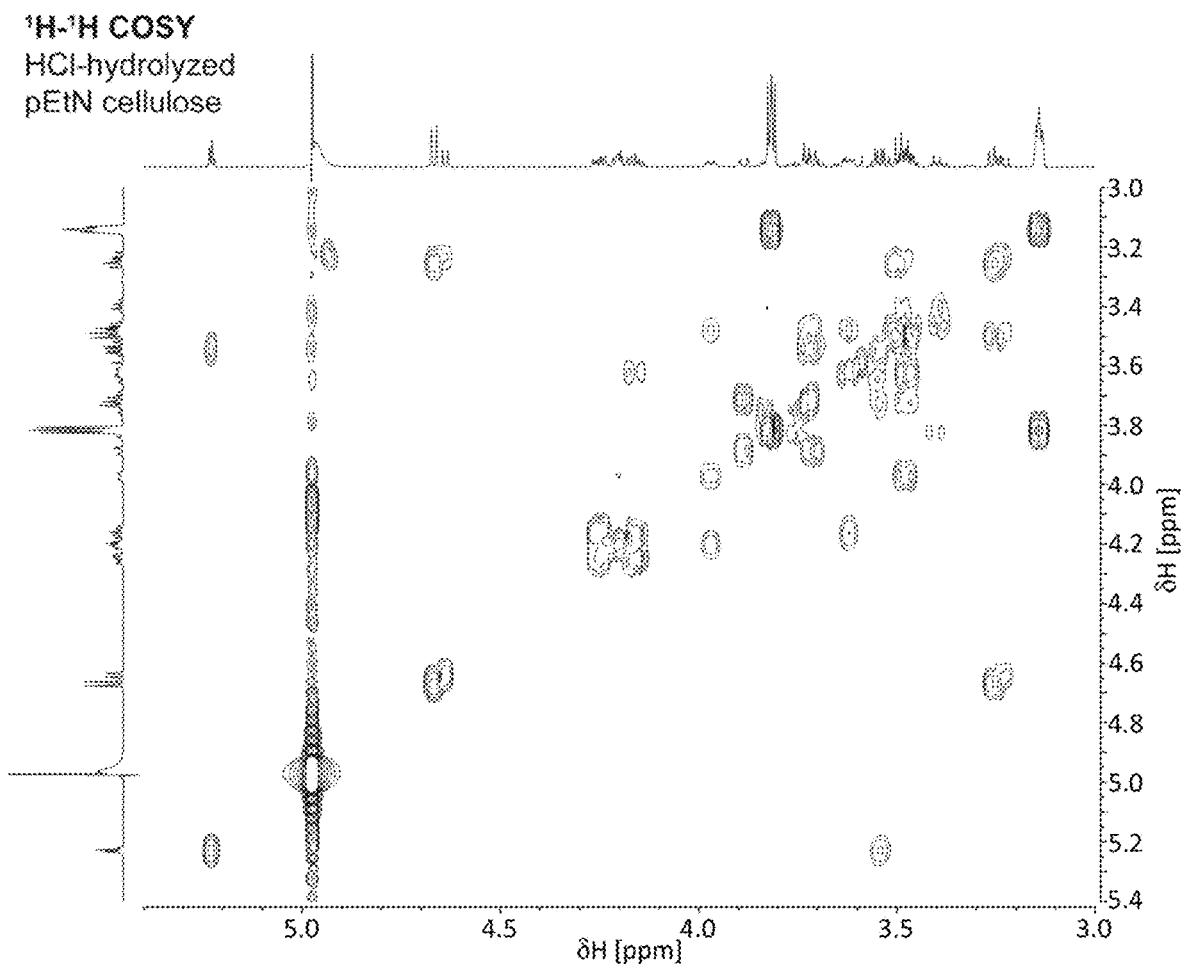
FIG. 9 shows $^1$H-$^1$H COSY NMR. The solution-state $^1$H-$^1$H COSY NMR spectrum of the acid-digested pEtN cellulose indicates the presence of glucose-6-phosphate, ethanolamine, and a minor amount of glucose. The spectrum was referenced to DSS.
Figure 10:
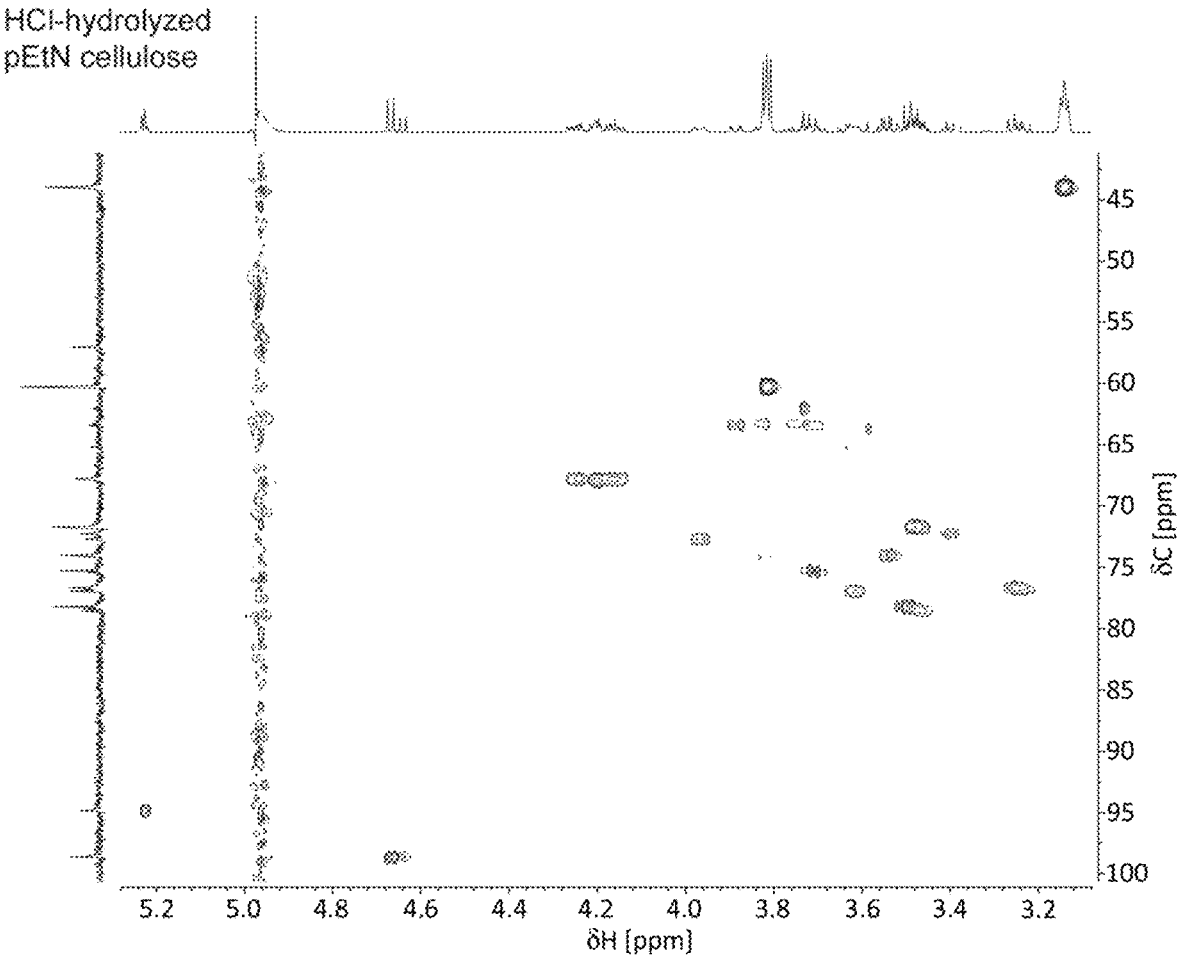
FIG. 10 shows $^1$H-$^{13}$C HSQC NMR. The solution-state $^1$H-$^{13}$C HSQC NMR spectrum of the acid-digested pEtN cellulose indicates the presence of glucose-6-phosphate, ethanolamine, and a minor amount of glucose. The spectrum was referenced to DSS.
Figure 11:
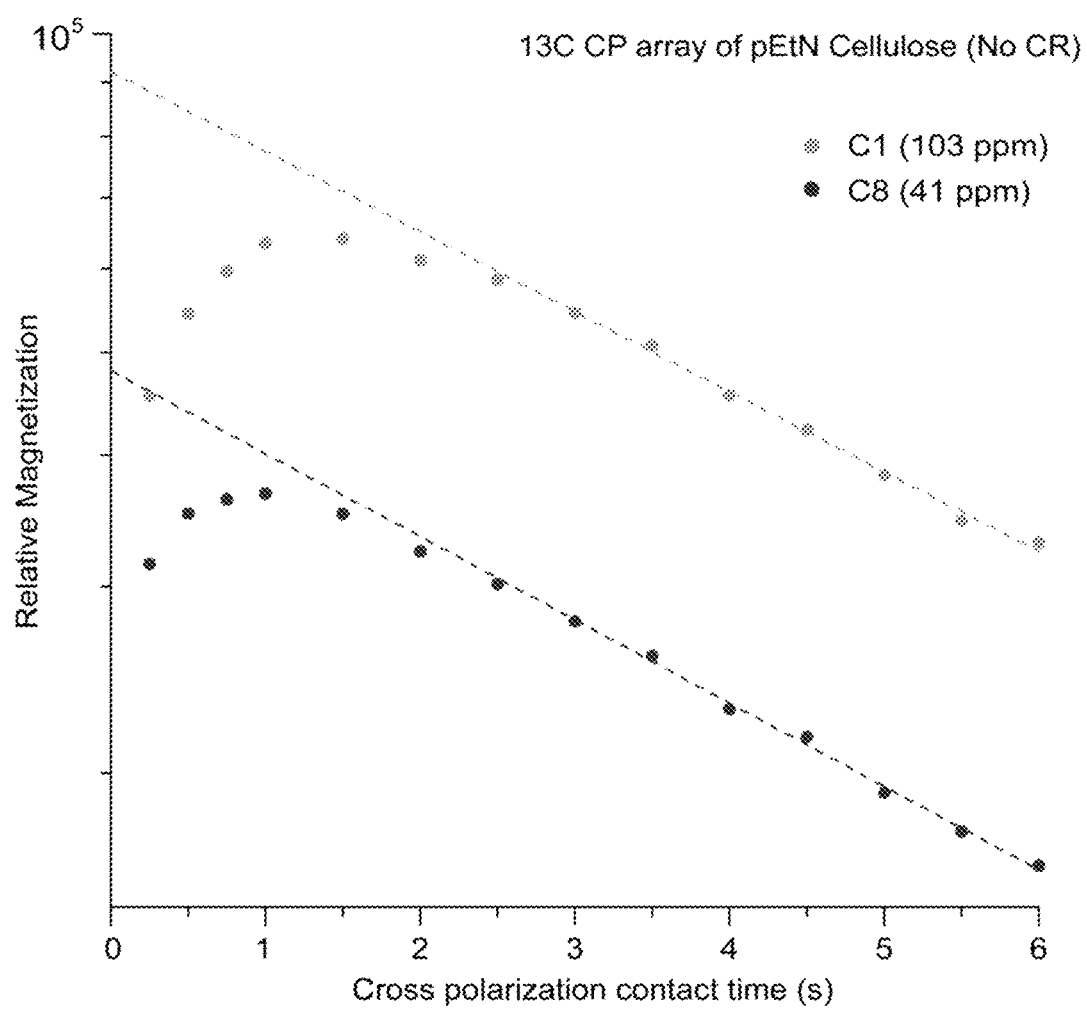
FIG. 11 shows that quantitative CP measurements yield a 1.9:1 ratio for the C1:C8 carbon peaks in pEtN cellulose.

Additional solution-state NMR analysis was performed on components released into solution after acid hydrolysis and supported the assignments from solid-state NMR. However, acid hydrolysis lead to degradation of the modification as well as precipitation of some of the material that was subsequently not assayed, observations that explain the difficulty of detecting the modified cellulose using conventional methods. Nevertheless, the two distinct modification carbons (C7 and C8) were observed in the solution NMR spectrum of acid digested material (FIG. 7). The C5 and C6 $^{13}$C chemical shifts in the modified glucose shifted upfield and downfield, respectively, as expected for a modification at C6 (FIG. 8). The complete set of $^{13}$C and $^1$H chemical shifts revealed the presence of soluble glucose, glucose-6-phosphate, and ethanolamine after hydrolysis and are provided in comparison with standard samples similarly referenced in acid (FIGS. 7 and 8). Solution-state $^1$H COSY and $^1$H-$^{13}$C HSQC spectra of the acid-hydrolyzed material additionally supported the assignments (FIGS. 9 and 10). Finally, a solid-state $^{13}$C CP array NMR experiment confirmed that approximately one half of the cellulose glucose units in the intact polymer are modified with pEtN on the glucose C6 carbon (FIG. 11).

Figure 1D:
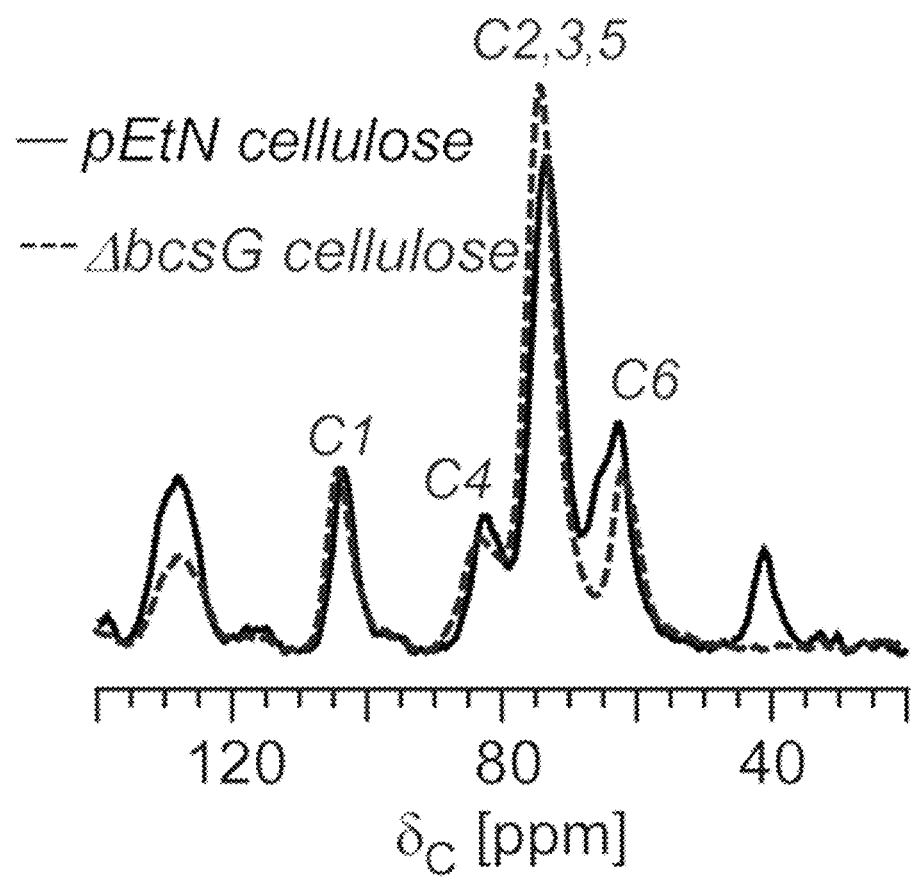

A biosynthetically modified cellulose has wide-ranging implications and potential applications. Among these, the specifically modified cellulose could be essential for the formation and function of bacterial biofilms containing the polymer; could exhibit attractive properties for new cellulosic materials; and potentially could be introduced into other organisms if gene-directed. Thus, we sought to identify the genes involved in the installation of the cellulose modification. The bcsEFG operon, which is part of the cellulose gene cluster in E. coli, had not been ascribed a definitive role in cellulose synthesis. The $^{13}$C CPMAS NMR comparison of the isolated cellulose from a ΔbcsG mutant revealed that the bcsG gene was indispensable for the cellulose modification (FIG. 1D). The spectrum lacks the contributions from the 41-ppm C8 carbon and the 63-ppm C7 carbon. As expected, the sugar C6 carbon contribution appears only at the upfield $^{13}$C position of 63 ppm, corresponding only to unmodified glucose. Complementation of the ΔbcsG mutant with bcsG on a plasmid restored production of the modified cellulose (FIG. 12). The prevalence of the modification was reduced in in-frame non-polar ΔbcsE and ΔbcsF mutants, indicating that BcsE and BcsF may play an accessory and possibly regulatory role in the installation of pEtN by BcsG (FIG. 13).

Biofilm production by wild-type E. coli involves the coproduction and tight association of amyloid curli fibers and what has been considered to be cellulose (Serra et al. (2013) mBio 4(2), e00103-00113; Serra et al. (2013) J. Bacteriol. 195, 5540-5554). Yet, we have now determined that the widely studied E. coli strains UTI89 and AR3110 produce pEtN cellulose. Thus, we sought to test whether this cellulose modification is functionally important for matrix assembly by evaluation of macrocolony morphotypes. BcsG is required for the wrinkling typically observed for the AR3110 macrocolonies. BcsG is also required for the formation of a pellicle, a biofilm formed at the air-liquid interface. Thus, pEtN modification of cellulose is required for community behavior exhibited when both curli and pEtN cellulose are co-produced.

BcsG is composed of 559 amino acids and has been predicted to be an integral membrane protein. A hydropathy plot analysis of BcsG supported the presence of several putative transmembrane spanning regions in the N-terminal 160 amino acids followed by a large hydrophilic C-terminal domain.

To date, we have developed a model in which BcsG acts as a phosphoethanolamine transferase, modifying cellulose after its emergence from the BcsA-BcsB machinery. The stoichiometry of the modification as occurring on approximately one half of the glucose units suggests that there is recognition of a disaccharide to result in modification of one glucose unit. A higher stoichiometry is possible.

Figure 2A:
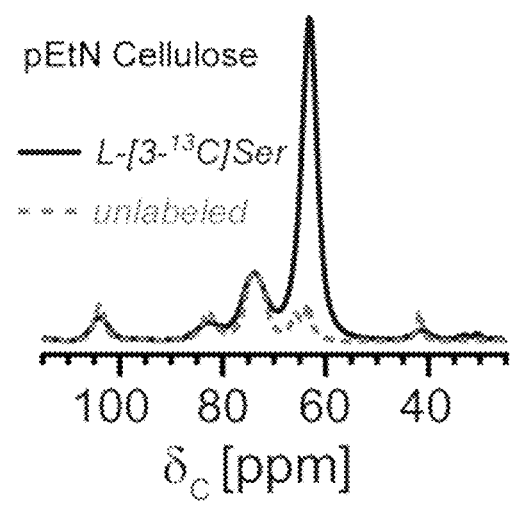
FIGS. 2A-2C show phosphoethanolamine cellulose production is detected in curli-integrated *E. coli* biofilm matrices with isotopic serine labeling and is also produced by *Salmonella enterica*.
Figure 2B:
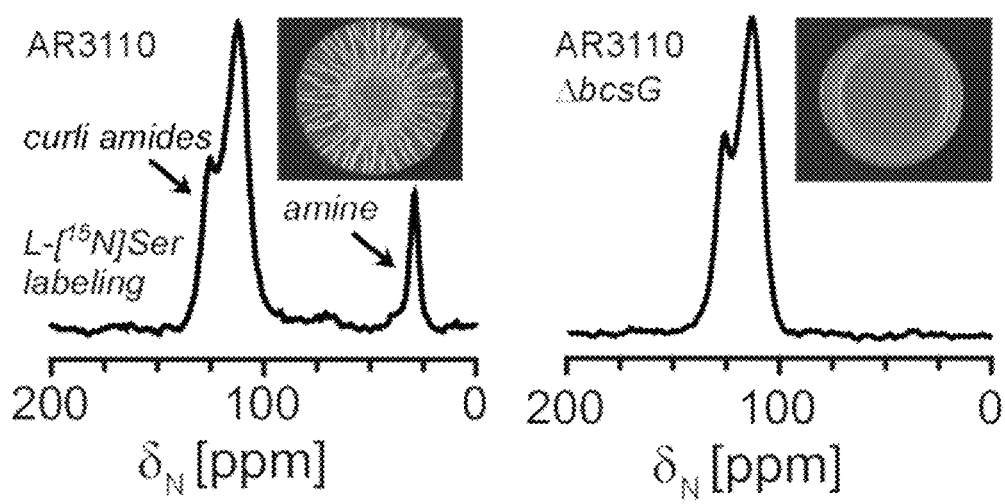
Figure 2C:
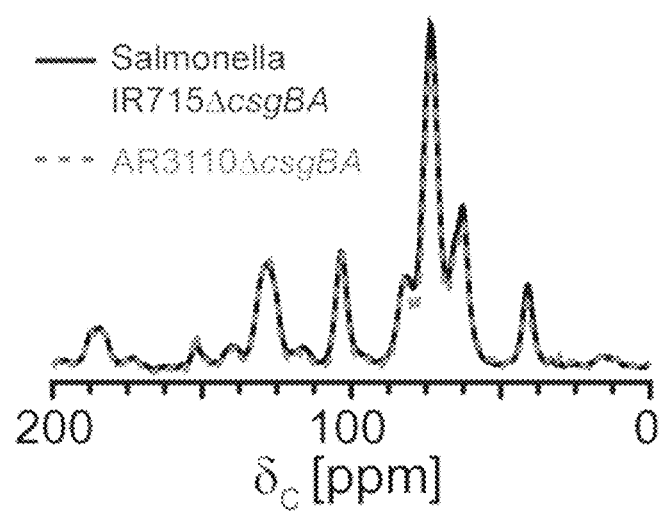

We also addressed the question of the substrate for BcsG-mediated PEtN modification of cellulose emerging from the BcsA-BcsB complex. We noticed that, with respect of overall size (559 and 563 residues, respectively) and length and transmembrane orientation of domains, BcsG resembles EptB, a phosphoethanolamine transferase using the phospholipid phosphatidylethanolamine (PE) to modify bacterial lipopolysaccharide (LPS) (Reynolds et al. (2005) J. Biol. Chem. 280, 21202-21211). We therefore hypothesized that pEtN modification by BcsG may also originate from PE. In this case the modified cellulose should have atoms derived from serine, which serves as a direct precursor for the ethanolamine moiety of PE. Thus, pEtN cellulose was prepared from cells grown on agar medium supplemented with 25 mg/L L-[3-$^{13}$C]Ser to detect whether pEtN cellulose would be enriched through incorporation of the serine label. The expected C7 carbon in the pEtN cellulose spectrum was indeed enhanced due to label incorporation from serine (FIG. 2A). The routing of serine into the modification is consistent with PE serving as a substrate for BcsG. Inspired by labeled serine incorporation, we sought to employ an isotopic labeling strategy that could identify whether pEtN cellulose was present in an intact extracellular matrix preparation with curli present in addition to the polysaccharide. The L-[3-$^{13}$C]Ser would not provide a unique signature for the modified cellulose as serine contributes significantly to the major curli subunit protein, CsgA. Thus, we employed L-[$^{15}$N]Ser labeling, anticipating an amine $^{15}$N contribution from pEtN cellulose resolved from curli amide signals. Inspection of the $^{15}$N CPMAS spectra of ECM isolated from AR3110 and AR3110ΔbcsG ECM revealed that the amine nitrogen resulting from L-[$^{15}$N]Ser labeling was due to the pEtN cellulose and was not observed in the AR3110ΔbcsG spectrum (FIG. 2B). The amide peaks associated with curli serine residues and also glycine through isotopic scrambling are present in both spectra. In this way, the potential presence of pEtN cellulose can be determined in intact ECM preparations from different E. coli strains and different organisms.

Finally, together with core cellulose genes, bcsEFG genes occur in many γ- and β-proteobacteria (Romling et al. (2015) Trends Microbiol. 23, 545-557). We isolated the cellulose material from Salmonella enterica serovar Typhimurium strain IR715ΔcsgBA (Tukel et al. (2005) Mol. Microbiol. 58, 289-304), a curli mutant, and discovered that it also produces pEtN cellulose. The $^{13}$C CPMAS NMR spectrum of isolated cellulose from Salmonella matches that of pEtN cellulose from E. coli (FIG. 2E). Thus, the pEtN modification of cellulose is likely to be common in the γ and β branches of proteobacteria. Bacterial species that do not possess bcsEFG genes but feature other accessory bcs genes of unknown function, could possibly use alternative modes of cellulose modification.

Modified cellulose is produced by strains that have been assumed in the literature to be producing standard amorphous cellulose based on simple Calcofluor staining procedures and conventional isolation methods designed for the detection of glucose from hydrolyzed cellulose.

However, these methods involve harsh hydrolysis protocols and crude purification or enrichment methods, followed by chromatography and mass spectrometry, and have not attempted a complete accounting of the intact material. Solid-state NMR analysis of the relevant intact polysaccharide was able to identify this biologically important pEtN modification that evaded detection by conventional approaches. PEtN cellulose is a newly identified zwitterionic polymer and, to our knowledge, our study provides the first definitive evidence so far of a naturally post-synthetically modified cellulose. In the extracellular matrix of bacterial biofilms, pEtN modification of cellulose, which allows enhanced network formation when coproduced with amyloid curli fibers. Thus, inhibition of BcsG could offer new opportunities to control biofilm formation, in particular by Gram-negative pathogens associated with infections and particularly serious and chronic infections. Furthermore, the identification of the gene-directed biosynthetic machinery also inspires the generation of engineered systems to produce alternately modified cellulose materials.

Materials and Methods

Bacterial Strains and Culture Conditions

The strains used in this study include laboratory E. coli K-12 strains W3110 and AR3110, Uropathogenic E. coli strain UTI89 (O18:K1:H7), and Salmonella enterica serovar Typhimurium strain IR715ΔcsgBA (Hayashi et al. (2006)

Mol. Syst. Biol. 2, 2006.0007). *E. coli* K-12 strain AR3110 is a direct derivative of W3110 (Hayashi et al., supra), in which codon 6 (the stop codon TAG) in the chromosomal copy of bcsQ was changed to the sense codon TTG (Serra et al. (2013) *J. Bacteriol.* 195, 5540-5554). Knockout mutations generated in AR3110 or W3110 are full open reading frame deletion/antibiotic resistance cassette insertions previously described (Serra et al. (2013) *J. Bacteriol.* 195, 5540-5554; Richter et al. (2014) *EMBO Mol. Med.* 6, 1622-1637). Mutations were transferred using P1 transduction (Miller, Experiments in molecular genetics. Cold Spring Harbor, N.Y.: Cold Spring Harbor Laboratory (1972)).

In order to grow macrocolony biofilms, 5 µl of an overnight cultures in LB medium were spotted on freshly prepared agar plates containing YESCA (Lim et al. (2014) *Biochem. Biophys. Res. Comm.* 443, 345-350) medium. Plates were supplemented with Congo red (40 µg/ml) and Coomassie Brilliant blue (20 µg/ml). Since cellulose and curli fiber expression occurs below 30° C. in *E. coli* K-12 derivatives, plate and liquid cultures were grown at 26° C. Photography of macrocolonies was previously described (Serra et al. (2013) mBio 4(2), e00103-00113).

ECM and Polysaccharide Isolation

Non-isotopically labeled NMR samples of cellulosic materials were prepared from UTI89ΔcsgA, AR3110ΔcsgBA, AR3110ΔcsgBAΔbcsE, AR3110ΔcsgBAΔbcsF, AR3110ΔcsgBAΔbcsG, AR3110ΔcsgBAΔbcsG/pBcsG, and SalmonellaIR715ΔcsgBA grown on YESCA agar supplemented with 25 µg/mL Congo red at 26° C. for 60 hours. Bacterial cells were scraped into a 10 mM Tris, pH 7.4 and sheared using an OmniMixer homogenizer for five cycles of one-minute shear and two-minute rest. Cells were pelleted by centrifugation at 5,000 g at 4° C. for 10 minutes and washed and pelleted two additional times in the Tris buffer. The resulting supernatants were spiked with 5M NaCl to achieve a final concentration of 170 mM NaCl. The ECM or cellulosic material was then pelleted down by centrifugation at 13,000 g for one hour. The pellets were subjected to 4% SDS treatment overnight and subsequently washed to remove all SDS.

Uniformly $^{15}$N-labeled pEtN cellulose was prepared as described above, but from cells grown on a modified version of Neidhardt's MOPS minimal agar medium supplemented with Congo red (McCrate et al. (2013) *J. Mol. Biol.* 425, 4286-4294). Serine labeled pEtN and ECM samples were prepared from cells grown on YESCA agar medium supplemented with 25 µg/mL Congo red and either 25 mg/L L-[3-$^{13}$C]Ser or L-[$^{15}$N]Ser.

PEtN cellulose was purified without Congo red using a strain engineered to overexpress diguanylate cyclase to increase the yield of isolated material. The pEtN cellulose overproducing strain UTI89ΔcsgA/pMMB956 was created by transforming UTI89ΔcsgA with pMMB956, a plasmid overexpressing diguanylate cyclase under IPTG induction. The bacteria were grown at 26° C. for 60 hours on YESCA agar containing 250 µM of IPTG. Bacterial cells were harvested into 10 mM Tris, pH 7.4 and sheared using an OmniMixer homogenizer for five cycles of one-minute shear and two-minute rest. Cells were pelleted by centrifugation at 5,000 g for 10 minutes and washed and pelleted two additional times in the Tris buffer. The resulting supernatants were dialyzed using 100 kDa dialysis membrane against water overnight. The dialyzed solutions were frozen, thawed, and centrifuged at 10,000 g at 4° C. for 20 minutes to pellet the cellulosic material. The cellulosic materials were subjected to 4% SDS treatment overnight and then washed to remove all SDS.

Solid-State NMR Experiments

All the $^{13}$C CPMAS, $^{15}$N CPMAS, $^{13}$C CP array and C{N} REDOR experiments were performed using an 89-mm wide-bore Varian magnet at 11.7T (499.12 MHz for $^{1}$H and 125.52 MHz for $^{13}$C) and a home-built four-frequency transmission-line probe with a 13.66-mm-long, 6-mm inner diameter sample coil, and a Revolution NMR MAS Vespel stator. Samples were spun in thin-wall 5 mm outer diameter zirconia rotors (Revolution NMR, LLC) at 7143±2 Hz using a Varian MAS control unit. For all NMR experiments, the it-pulse lengths were 7 µs for $^{1}$H and 10 µs for $^{13}$C and $^{15}$N. The recycle delay was 2 s. The proton-carbon and the proton-nitrogen cross polarizations occurred at 50 kHz for 1.5 ms unless otherwise noted. The $^{13}$C spectra were referenced to TMS as 0.0 ppm, which was determined relative to an adamantine standard at 38.5 ppm. The $^{15}$N spectra were referenced to liquid ammonia at 0 ppm.

The $^{31}$P CPMAS and C{P} REDOR spectra were obtained using a 500 MHz spectrometer with an 89 mm-bore Magnex magnet; a six-frequency transmission-line probe having a 12-mm long, 6-mm inside-diameter analytical coil housed in a Chemagnetics/Varian magic-angle spinning ceramic stator, controlled by a Tecmag pulse programmer; and active feedback control of high-power amplifiers. $^{1}$H-$^{13}$C cross-polarization transfers were made with radiofrequency fields of 62.5 kHz. The it-pulse lengths were 8 µs for $^{13}$C and 9 µs for $^{31}$P. Proton dipolar decoupling was 100 kHz with TPPM modulation (Bennett et al. (1995) *J. Chem. Phys.* 103, 6951-6958) during dipolar evolution and data acquisition.

Solution-state NMR Experiments 5 mg/mL of pEtN cellulose was digested in 0.5 M HCl in D$_2$O at 95° C. for 48 hours. Brown precipitates were observed and pelleted down by centrifugation at 5,000 g for 5 minutes. 700 µL of the supernatant was transferred to a solution NMR tube and DSS was added in as a chemical shift reference standard. $^{1}$H NMR spectra of the hydrolyzed pEtN cellulose and control samples of ethanolamine, glucose and glucose-6-phosphate were collected on a 600 MHz Varian NMR spectrometer with water suppression using a pre-saturation method. $^{13}$C NMR spectra were collected on a 500 MHz Varian NMR spectrometer. $^{1}$H-$^{1}$H COSY and $^{1}$H-$^{13}$C HSQC of the hydrolyzed pEtN cellulose were measured on a 600 MHz Varian NMR spectrometer. The intact pEtN cellulose sample analyzed by solution-state NMR was prepared by adding D$_2$O to lyophilized pEtN cellulose and sonicating briefly prior to the $^{1}$H NMR measurement on a 600 MHz Varian NMR spectrometer.

Construction of Translational lacZ and phoA Reporters and Enzyme Assays

Plasmids for the expression of translational lacZ or phoA fusions to bcsF and bcsG were constructed using oligonucleotide primers listed in Table 1 and pJL28 (Lucht et al. (1994) *J. Biol. Chem.* 269, 6578-6586) or pAP28 as a vector. pAP28 is a phoA translational fusion vector based on pJL28 in which part of lacZ was removed via HindIII/EcoRV digestion and then replaced by the phoA sequence without its signal sequence-encoding 5'-part (using oligos FMO-68/-69 listed in Table 1).

β-galactosidase (LacZ) activity was determined using o-nitrophenyl-β-D-galactopyranoside (ONPG) as a substrate and is reported as µmol of o-nitrophenol per min per mg of cellular protein. Alkaline phosphatase (PhoA) activity was determined using p-nitrophenyl-phosphate (pNPP) as a substrate and is reported as µmol of p-nitrophenol per min per mg of cellular protein. All enzyme assays were done at least in triplicate with average data and standard deviations shown in the respective figures.

TABLE 1

Oligonucleotide primers used in the present study.
I. Primers used generating translational lacZ and phoA fusions:

| | |
|---|---|
| FMO-68 (HindIII) | TAAATAAGCTTCGGACACCAGAAATGCC (SEQ ID NO:1) |
| FMO-69 (EcoRV) | TAAATGATATCTTAAGTCTGGTTGCTAACAGC (SEQ ID NO:2) |
| bcsEFG-BamHI | GGCCCGGGATCCCTGGAAGATATAGCCTATCGC (SEQ ID NOG) |
| bcsF+3-phoA-HindIII | GGCCCGAAGCTTCATGATGAGCGCTCCACAG (SEQ ID NOG) |
| bcsF+72-phoA-HindIII | GGCCCGAAGCTTCAGATAGCCCAGCGGGAAAA (SEQ ID NOG) |
| bcsG+3-phoA-HindIII | GGCCCGAAGCTTCATTTTTTGGTTGCCCTGGC (SEQ ID NOG) |
| bcsG+474-phoA-HindIII | GGCCCGAAGCTTACTTGGTCCCGCCAGGGTA (SEQ ID NO:7) |
| bcsF+4-lacZ-HindIII | GGCCCGAAGCTTTCATGATGAGCGCTCCACAG (SEQ ID NOG) |
| bcsF+73-lacZ-HindIII | GGCCCGAAGCTTCCAGATAGCCCAGCGGGAA (SEQ ID NO:9) |
| bcsG+4-lacZ-HindIII | GGCCCGAAGCTTTCATTTTTTGGTTGCCCTGGC (SEQ ID NO: 10) |
| bcsG+487-lacZ-HindIII | GGCCCGAAGCTTGCCACAAGGAGAAACTTGGTC (SEQ ID NO: 11) |

Example 2

Production of Non-Modified Cellulose by *E. Coli* Lacking the csgG Gene

The AR3110ΔcsgBAΔbcsG mutants were grown on Congo red-supplemented YESCA agar to qualitatively evaluate cellulose production. The Congo red serves as an indicator of both unmodified cellulose and modified cellulose production. Congo red binding by the AR3110ΔcsgBA mutant is attributed only to cellulose as it does not produce curli. AR3110ΔcsgBAΔbcsG exhibited Congo red binding that was comparable to AR3110ΔcsgBA, whereas Congo red binding was abrogated in the bcsE and bcsF derivatives, which influence the amount of production of cellulosic material (FIG. 15). Thus, the AR310ΔcsgBAΔbcsG mutant produced significant quantities of unmodified cellulose when the cells were grown on nutrient agar medium. The absence of the normal biofilm phenotype (wrinkling on agar and pellicle formation at the air-liquid interface) is not due to failure of the mutant cells to make cellulosic material (the mutant makes regular cellulose as confirmed by NMR), but rather, the lack of the phosphoethanolamine modification.

Example 3

The Phosphoethanolamine Modification Enhances Solubility in Water

The solubility of purified *E. coli* phosphoethanolamine cellulose in water was compared with commercially available crystalline cellulose and commercially available carboxymethyl cellulose (produced chemically), with the latter known to be soluble in water and highly digestible by cellulases. The zwitterionic phosphoethanolamine cellulose was found to be semi-soluble in water and significantly more soluble than unmodified cellulose (FIG. 16). Its enhanced solubility indicates that phosphoethanolamine cellulose will be useful in numerous applications that currently utilize other synthetically modified celluloses.

Example 4

The Phosphoethanolamine Cellulose is More Digestible by Cellulase

*Aspergillus niger* cellulase was used for enzymatic hydrolysis of phosphoethanolamine cellulose, crystalline cellulose, and commercially available carboxymethyl cellulose. The glucose produced by hydrolysis was detected with a standard hexokinase assay. As shown in FIG. 17, the phosphoethanolamine cellulose produced by *E. coli* was more digestible by cellulase than commercial crystalline cellulose. Thus, treatment of cellulose with the BcsG-encoded phosphoethanolamine transferase renders cellulose more digestible. The transfer of the bcsG gene, by itself or in combination with the bcsE and bcsF genes may enable the production of phosphoethanolamine cellulose in plants and other organisms. The phosphoethanolamine modification of cellulose may weaken associations with lignin or other components and aid in efforts to digest cellulosic material for applications including the conversion of cellulose and cellulosic materials into ethanol.

Although preferred embodiments of the subject invention have been described in some detail, it is understood that obvious variations can be made without departing from the spirit and the scope of the invention as defined herein.

What is claimed is:

1. A method of producing phosphoethanolamine cellulose, the method comprising:
   a) culturing an *Escherichia* or a *Salmonella* host cell comprising a recombinant polynucleotide encoding a BcsG phosphoethanolamine transferase comprising the amino acid sequence of SEQ ID NO:12 or SEQ ID NO:13 operably linked to a promoter under conditions suitable for expression of the BcsG phosphoethanolamine transferase, wherein the phosphoethanolamine cellulose is produced; and
   b) isolating the phosphoethanolamine cellulose.

2. The method of claim 1, wherein the BcsG phosphoethanolamine transferase is exogenous.

3. The method of claim 1, wherein said culturing is performed at a temperature in a range from about 25° C. to about 37° C.

4. The method of claim 1, wherein the cellulose-producing *Escherichia* or *Salmonella* host cell is supplied with a growth media using a continuous or batch fed system.

5. The method of claim 1, wherein said culturing is performed in a growth media comprising one or more carbon sources selected from the group consisting of glucose, fructose, acetate, or glycerol.

6. The method of claim 1, further comprising increasing cellulose production by contacting the cellulose-producing host cell with cyclic di-GMP.

7. The method of claim 1, wherein the recombinant polynucleotide is provided by a vector or integrated into the host cell genome.

8. The method of claim 1, wherein the *Escherichia* or *Salmonella* host cell further comprises a recombinant polynucleotide comprising a BcsE gene or a BcsF gene operably linked to a promoter.

9. The method of claim 1, wherein the recombinant polynucleotide comprises a bcsEFG operon encoding the BcsG phosphoethanolamine transferase.

10. The method of claim 1, wherein the *Escherichia* or *Salmonella* host cell is selected from the group consisting of *Escherichia coli* and *Salmonella enterica*.

11. The method of claim 1, further comprising esterifying the isolated phosphoethanolamine cellulose to produce a phosphoethanolamine cellulose ester, wherein at least one hydroxyl group of the phosphoethanolamine cellulose is esterified.

12. The method of claim 11, wherein said esterifying comprises reacting the phosphoethanolamine cellulose with an organic acid, an acid anhydride, an acid chloride, or an inorganic acid.

13. The method of claim 12, wherein the organic acid is selected from the group consisting of acetic acid, propanoic acid, and butyric acid.

14. The method of claim 12, wherein the inorganic acid is selected from the group consisting of nitric acid and sulfuric acid.

15. The method of claim 1, further comprising etherification of the isolated phosphoethanolamine cellulose to produce a phosphoethanolamine cellulose ether, wherein at least one hydroxyl group of the phosphoethanolamine cellulose is etherified.

16. The method of claim 15, wherein the phosphoethanolamine cellulose ether is an alkyl ether, a hydroxyalkyl ether, or a carboxyalkyl ether.

17. The method of claim 1, further comprising modifying at least one amine group of the isolated phosphoethanolamine cellulose.

18. The method of claim 17, wherein said at least one amine group is alkylated, acylated, sulfonated, or conjugated to an agent.

19. The method of claim 18, wherein the agent is a peptide, antibody, enzyme, nucleic acid, dye, ligand, or drug.

* * * * *